US011241195B2

(12) United States Patent
McFarlin et al.

(10) Patent No.: US 11,241,195 B2
(45) Date of Patent: Feb. 8, 2022

(54) SYSTEM AND METHOD FOR EVOKING A REFLEX TO MONITOR THE NERVES OF THE LARYNX

(71) Applicant: Medtronic Xomed, Inc., Jacksonville, FL (US)

(72) Inventors: Kevin L. McFarlin, Saint Johns, FL (US); David C. Hacker, Jacksonville, FL (US); Anirudhan Narasimhan, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 450 days.

(21) Appl. No.: 16/108,682

(22) Filed: Aug. 22, 2018

(65) Prior Publication Data

US 2019/0059813 A1 Feb. 28, 2019

Related U.S. Application Data

(60) Provisional application No. 62/548,739, filed on Aug. 22, 2017, provisional application No. 62/644,957, filed on Mar. 19, 2018.

(51) Int. Cl.
*A61B 5/00* (2006.01)
*A61M 16/04* (2006.01)
(Continued)

(52) U.S. Cl.
CPC .............. *A61B 5/4893* (2013.01); *A61B 5/24* (2021.01); *A61B 5/296* (2021.01); *A61M 16/022* (2017.08);
(Continued)

(58) Field of Classification Search
CPC ...... A61N 1/0519; A61N 1/0517; A61N 1/05; A61N 1/0556; A61N 1/3601; A61N 1/056;
(Continued)

(56) References Cited

U.S. PATENT DOCUMENTS

| 1,864,688 A | 6/1932 | Frank |
| 2,107,835 A | 2/1938 | Pierce |

(Continued)

FOREIGN PATENT DOCUMENTS

| WO | 2007078827 | 7/2007 |
| WO | 2008091928 | 7/2008 |

(Continued)

OTHER PUBLICATIONS

Jain, A.K., Sharma, P.K. and Bhattacharya, A. (1995), Double burst stimulation for monitoring neuromuscular blockade for tracheal intubation. Anaesthesia, 50: 23-25. https://doi.org/10.1111/j.1365-2044.1995.tb04507.x (Year: 1995).*
International Search Report and Written Opinion, PCT/US2018/047491 dated Nov. 27, 2018 (14 pages).
Ludlow, Christy L., "Central Nervous System Control of the Laryngeal Muscles in Humans", Respiratory Physiology & Neurobiology 147 (2005) 205-222.

(Continued)

*Primary Examiner* — Sean P Dougherty
*Assistant Examiner* — Benjamin S Melhus
(74) *Attorney, Agent, or Firm* — Dicke, Billig & Czaja, PLLC

(57) ABSTRACT

A system includes an endotracheal tube having a plurality of electrodes, wherein the electrodes include at least one stimulating electrode configured to stimulate tissue of a patient and at least one monitoring electrode configured to monitor at least one nerve of a patient. The system includes a nerve integrity monitor device configured to send a stimulation signal to the at least one stimulating electrode to evoke a reflex response, and configured to receive a monitoring signal from the at least one monitoring electrode.

20 Claims, 15 Drawing Sheets

(51) Int. Cl.
*A61B 5/0492* (2006.01)
*A61B 5/04* (2006.01)
*A61N 1/05* (2006.01)
*A61M 16/00* (2006.01)
*A61B 5/24* (2021.01)
*A61B 5/296* (2021.01)
*A61B 5/394* (2021.01)
*A61N 1/36* (2006.01)

(52) U.S. Cl.
CPC ........ *A61M 16/04* (2013.01); *A61M 16/0434* (2013.01); *A61N 1/0519* (2013.01); *A61B 5/394* (2021.01); *A61B 5/6853* (2013.01); *A61M 16/0402* (2014.02); *A61M 16/0443* (2014.02); *A61M 2205/054* (2013.01); *A61M 2205/3303* (2013.01); *A61M 2205/50* (2013.01); *A61M 2205/581* (2013.01); *A61M 2205/583* (2013.01); *A61M 2205/8206* (2013.01); *A61N 1/3601* (2013.01)

(58) Field of Classification Search
CPC ............ A61N 1/36114; A61N 1/36007; A61N 1/36185; A61N 1/0456; A61N 1/0472; A61N 1/0502; A61N 1/0526; A61N 1/0551; A61N 1/36017; A61N 1/36031; A61N 1/36034; A61N 1/362; A61N 1/3686; A61N 7/02; A61N 1/04; A61N 1/0408; A61N 1/0452; A61N 1/0476; A61N 1/0484; A61N 1/0529; A61N 1/0534; A61N 1/0553; A61N 1/0558; A61N 1/06; A61N 1/08; A61N 1/086; A61N 1/325; A61N 1/327; A61N 1/36014; A61N 1/3605; A61N 1/3606; A61N 1/36071; A61N 1/3611; A61N 1/36139; A61N 1/3621; A61N 1/3625; A61N 1/3629; A61N 1/37211; A61N 1/37282; A61N 1/3752; A61N 1/3754; A61N 1/385; A61N 1/3918; A61N 1/40; A61N 7/00; A61N 7/022
See application file for complete search history.

(56) References Cited

U.S. PATENT DOCUMENTS

| | | | |
|---|---|---|---|
| 2,429,585 A | 10/1947 | Rogoff | |
| 2,618,684 A | 11/1952 | Bergan | |
| 2,872,505 A | 2/1959 | Ustin | |
| 3,165,575 A | 1/1965 | Lynch, Jr. et al. | |
| 3,494,364 A | 2/1970 | Peters | |
| 3,734,094 A | 5/1973 | Calinog | |
| 3,783,178 A | 1/1974 | Philibert et al. | |
| 3,892,455 A | 7/1975 | Sotolongo | |
| 4,304,239 A | 12/1981 | Perlin | |
| 4,369,794 A | 1/1983 | Furler | |
| 4,647,713 A | 3/1987 | deNijis et al. | |
| 4,776,808 A | 10/1988 | Davidson | |
| 5,096,445 A | 3/1992 | Lostumo | |
| 5,125,406 A | 6/1992 | Goldstone et al. | |
| 5,135,001 A | 8/1992 | Sinofsky et al. | |
| 5,429,617 A | 7/1995 | Hammersmark et al. | |
| 5,464,404 A | 11/1995 | Abela et al. | |
| 5,584,290 A | 12/1996 | Brain | |
| 5,782,774 A | 7/1998 | Shmulewitz | |
| 5,785,051 A | 7/1998 | Lipscher et al. | |
| 5,836,874 A | 11/1998 | Swanson et al. | |
| 5,864,093 A | 1/1999 | Hecock et al. | |
| 6,062,223 A | 5/2000 | Palazzo et al. | |
| 6,148,222 A | 11/2000 | Ramsey, III | |
| 6,226,548 B1 | 5/2001 | Foley et al. | |
| 6,259,938 B1 | 7/2001 | Zarychta et al. | |
| 6,266,549 B1 | 7/2001 | Melnikoff et al. | |
| 6,332,156 B1 | 12/2001 | Cho et al. | |
| 6,334,068 B1 | 12/2001 | Hacker | |
| 6,357,447 B1 | 3/2002 | Swanson et al. | |
| 6,439,232 B1 | 8/2002 | Brain | |
| 6,547,788 B1 | 4/2003 | Maguire et al. | |
| 6,584,347 B1 | 6/2003 | Sinderby | |
| 6,626,841 B1 | 9/2003 | Atlee, III | |
| 6,626,899 B2 | 9/2003 | Houser et al. | |
| 7,153,146 B2 | 12/2006 | Shimizu et al. | |
| 7,583,991 B2 | 9/2009 | Rea | |
| 7,736,362 B2 | 6/2010 | Eberl et al. | |
| 7,794,256 B1 | 9/2010 | Sochor | |
| 7,972,308 B2 | 7/2011 | Putz | |
| 8,145,289 B2 | 3/2012 | Calabro et al. | |
| 8,152,803 B2 | 4/2012 | Edwards et al. | |
| 8,224,422 B2 | 7/2012 | Mottola et al. | |
| 8,352,012 B2 | 1/2013 | Besio | |
| 8,467,844 B2 | 6/2013 | Rea et al. | |
| 9,084,551 B2 | 7/2015 | Brunnett et al. | |
| 9,763,624 B2 | 9/2017 | Stanislaus et al. | |
| 9,918,675 B2 | 3/2018 | Hacker et al. | |
| 9,918,676 B2 | 3/2018 | Hacker | |
| 10,058,669 B2 | 8/2018 | Razavi et al. | |
| 2001/0018281 A1 | 8/2001 | Royer | |
| 2002/0016615 A1 | 2/2002 | Dev et al. | |
| 2002/0032468 A1 | 3/2002 | Hill et al. | |
| 2003/0074039 A1 | 4/2003 | Puskas | |
| 2004/0186461 A1 | 9/2004 | DiMatteo | |
| 2005/0085111 A1 | 4/2005 | Clark et al. | |
| 2005/0222656 A1 | 10/2005 | Wahlstrand et al. | |
| 2007/0137651 A1 | 6/2007 | Glassenberg et al. | |
| 2007/0142888 A1 | 6/2007 | Chavez | |
| 2007/0219551 A1 | 9/2007 | Honour et al. | |
| 2008/0177190 A1 | 7/2008 | Libbus et al. | |
| 2008/0249507 A1 | 10/2008 | Hadani | |
| 2008/0255441 A1 | 10/2008 | Hadani | |
| 2008/0300650 A1 | 12/2008 | Gerber et al. | |
| 2009/0018611 A1* | 1/2009 | Campbell | A61N 1/0484 607/48 |
| 2009/0076561 A1* | 3/2009 | Libbus | A61N 1/36114 607/11 |
| 2009/0227885 A1 | 9/2009 | Lowery et al. | |
| 2010/0168561 A1 | 7/2010 | Anderson | |
| 2010/0168743 A1 | 7/2010 | Stone et al. | |
| 2010/0179417 A1 | 7/2010 | Russo | |
| 2010/0198099 A1 | 8/2010 | Murphy et al. | |
| 2010/0249639 A1 | 9/2010 | Bhatt | |
| 2010/0317956 A1 | 12/2010 | Kartush | |
| 2011/0071379 A1 | 3/2011 | Rea et al. | |
| 2011/0190596 A1* | 8/2011 | Hacker | A61M 16/0443 600/301 |
| 2011/0230734 A1 | 9/2011 | Fain et al. | |
| 2011/0301587 A1 | 12/2011 | Deem | |
| 2011/0306861 A1 | 12/2011 | Thramann et al. | |
| 2012/0016256 A1 | 1/2012 | Mabary et al. | |
| 2012/0178999 A1* | 7/2012 | Takeda | A61B 1/267 600/188 |
| 2013/0053926 A1* | 2/2013 | Hincapie Ordonez | A61N 1/36053 607/62 |
| 2014/0107524 A1* | 4/2014 | Brull | A61B 5/0488 600/554 |
| 2014/0275914 A1 | 9/2014 | Li et al. | |
| 2015/0164354 A1* | 6/2015 | Parker | A61N 1/36135 600/554 |
| 2016/0038073 A1 | 2/2016 | Brown et al. | |
| 2016/0038074 A1* | 2/2016 | Brown | A61B 5/0004 600/380 |
| 2016/0067485 A1 | 3/2016 | Lindenthaler et al. | |
| 2016/0262699 A1 | 9/2016 | Goldstone et al. | |
| 2016/0287112 A1 | 10/2016 | McFarlin et al. | |
| 2016/0287861 A1 | 10/2016 | McFarlin et al. | |
| 2016/0324475 A1 | 11/2016 | Hacker | |

(56) References Cited

U.S. PATENT DOCUMENTS

2016/0345905 A1    12/2016   Li
2020/0179676 A1*   6/2020   Sinclair ................ A61B 5/6853

FOREIGN PATENT DOCUMENTS

| WO | 2011041690 | | 4/2011 |
|----|------------|---|--------|
| WO | 2013008106 | | 1/2013 |
| WO | 2014105759 | A1 | 7/2014 |
| WO | 2018119454 | A1 | 6/2018 |

OTHER PUBLICATIONS

Sasaki et al., "Central Facilitation of the Glottic Closure Reflex in Humans", Ann Otol Rhino Laryngol 112:2003.

Kim et al., "Characteristics of Glottic Closure Reflex in a Canine Model", Yonsei Med J, vol. 50, No. 3, Jun. 2009, 380-384.

Sinclair et al., "A Novel Methodology for Assessing Laryngeal and Vagus Nerve Integrity in Patients under General Anesthesia", Clinical Neurophysiology 128 (2017) 1399-1405.

Sinclair et al., "Contralateral R1 and R2 Components of the Laryngeal Adductor Reflex in Humans Under General Anesthesia", Laryngoscope 2017, 127:12 (E443-E448).

* cited by examiner

SYSTEM AND METHOD FOR EVOKING A REFLEX TO MONITOR THE NERVES OF THE LARYNX

CROSS-REFERENCE TO RELATED APPLICATIONS

This Non-Provisional patent application claims the benefit of the filing dates of U.S. Provisional Patent Application Ser. No. 62/548,739, filed Aug. 22, 2017, and U.S. Provisional Patent Application Ser. No. 62/644,957, filed Mar. 19, 2018, the entire teachings of which are incorporated herein by reference.

BACKGROUND

During head and neck procedures such as thyroidectomy, neck dissection, intracranial procedures, and anterior cervical disc fusion, the nerves innervating the larynx are at risk of iatrogenic injury. Methods for monitoring these nerves to prevent injury may include evoked potential electromyography (EMG) recording systems.

Endotracheal tubes include electrodes that are designed to make contact with a patient's laryngeal musculature and vocal cords to facilitate EMG monitoring of the vocal cords during surgery when connected to an EMG monitoring device. Endotracheal tubes provide an open airway for patient ventilation, and provide for monitoring of EMG activity of the intrinsic laryngeal musculature when connected to an appropriate EMG monitor. Endotracheal tubes can provide continuous monitoring of the nerves supplying the laryngeal musculature during surgical procedures.

Information regarding anatomy and physiology of the larynx may be found in Sasaki, C; Anatomy and development and physiology of the larynx; GI Motility online; 2006; doi:10.1038/gimo7; which is hereby incorporated by reference herein.

SUMMARY

One embodiment is directed to a system that includes an endotracheal tube having a plurality of electrodes, wherein the electrodes include at least one stimulating electrode configured to stimulate tissue of a patient and at least one monitoring electrode configured to monitor at least one nerve of a patient. The system includes a nerve integrity monitor device configured to send a stimulation signal to the at least one stimulating electrode to evoke a reflex response, and configured to receive a monitoring signal from the at least one monitoring electrode.

DETAILED DESCRIPTION

During head and neck procedures, evoked potential electromyography (EMG) recording systems may require the surgeon to intermittently contact the individual nerve branches and nerve trunks with an electrical stimulation probe, thus, evoking a nerve action potential and subsequent muscle response that can be recorded using an electrical or mechanical sensor. Additionally, the surgeon may place an electrode on or near the trunk of the nerve. This electrode can periodically stimulate the nerve while the monitor tracks the muscle response. If the trended responses deviate or degrade significantly, the system can alert the surgeon, and the surgeon may choose to alter his or her approach or stop the procedure to prevent further nerve injury.

Embodiments disclosed herein are directed to devices and methods for evoked potential recording of the laryngeal nerves by eliciting laryngeal reflexes. Some embodiments evoke nerve potentials and subsequent muscle responses of the vocal folds by means of the protective reflexes of the upper airway. Some embodiments use electrical stimulation to evoke a reflex response that may be used to continuously monitor nerves of the head and neck. Some embodiments evoke these reflexes by electrically stimulating the mucosa (pharynx, supraglottic, glotic, subglottic) of the larynx above, at, and below the vocal folds and recording the responses. In some embodiments, the mucosa of the larynx is stimulated with the left electrodes (stimulation electrodes)

of an EMG endotracheal tube, and the response is recorded using the right electrodes (monitoring or recording electrodes) of the EMG tube. In some embodiments, the stimulation uses paired/multi pulse train stimuli with an interstimulus interval (ISI) of 2-5 ms.

Figure 1:
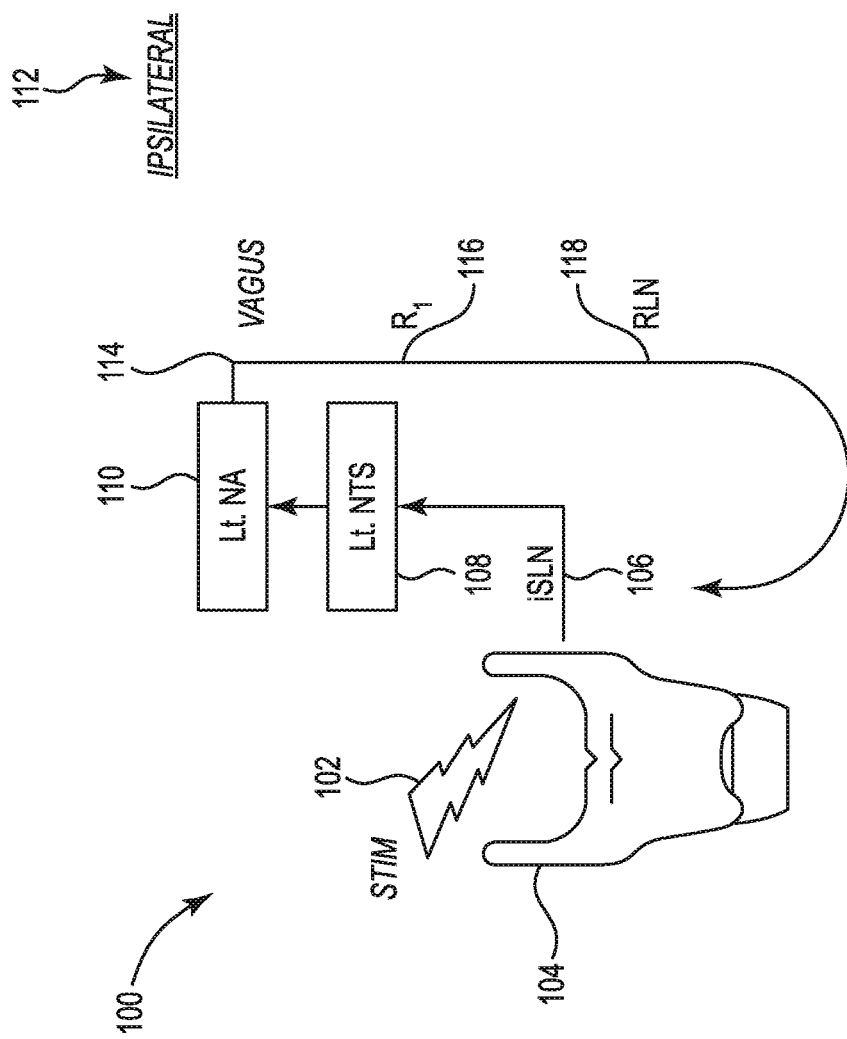
FIG. 1 is a diagram illustrating a laryngeal reflex algorithm according to one embodiment.

FIG. 1 is a diagram illustrating a laryngeal reflex algorithm 100 according to one embodiment. FIG. 1 shows an ipsilateral reflex 112. As shown in FIG. 1, stimulation (Stim) 102 is applied to larynx 104. Sensory nerve signals travel up the internal superior laryngeal nerve (iSLN) branch 106 of the vagus nerve 114 to the left nucleus tractus solitarius (Lt. NTS) 108 and the left nucleus ambiguus (Lt. NA) 110, which evoke a reflex ($R_1$) 116 that travels down the vagus nerve 114 to the recurrent laryngeal nerve (RLN) 118, which evokes muscle movement at the larynx 104.

Figure 2:
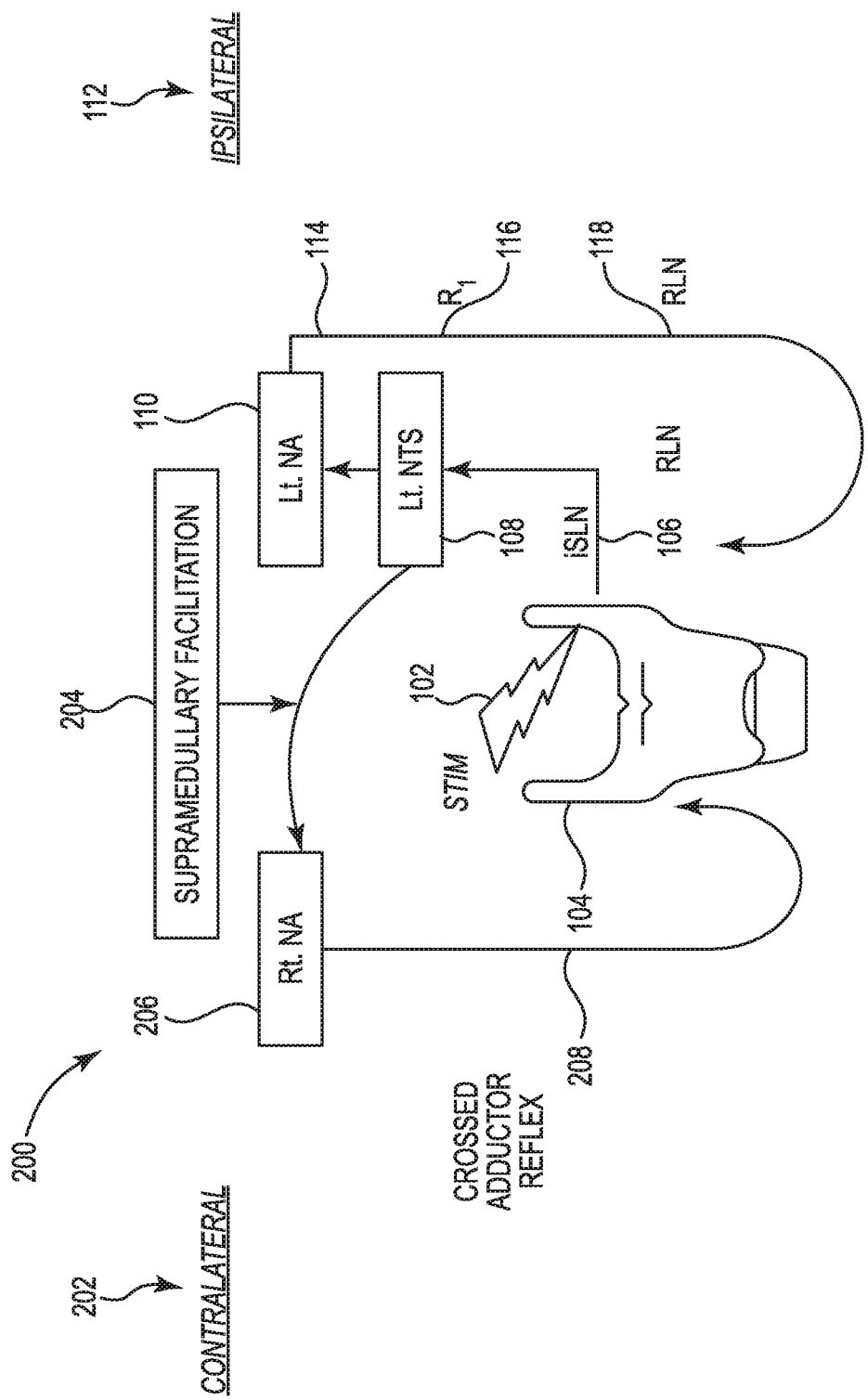
FIG. 2 is a diagram illustrating a normal response light anesthesia bilateral reflex according to one embodiment.

FIG. 2 is a diagram illustrating a normal response light anesthesia bilateral reflex 200 according to one embodiment. The bilateral reflex 200 includes a contralateral reflex 202 and an ipsilateral reflex 112. As shown in FIG. 2, stimulation (Stim) 102 is applied to larynx 104. Sensory nerve signals travel up the internal superior laryngeal nerve (iSLN) branch 106 of the vagus nerve 114 to the left nucleus tractus solitarius (Lt. NTS) 108 and the left nucleus ambiguus (Lt. NA) 110, which evoke a reflex ($R_1$) 116 that travels down the vagus nerve 114 to the recurrent laryngeal nerve (RLN) 118, which evokes muscle movement at the larynx 104. In addition, supramedullary facilitation 204 causes the right nucleus ambiguus (Rt. NA) 206 to evoke a crossed adductor reflex 208, which evokes muscle movement at the larynx 104.

Figure 3:
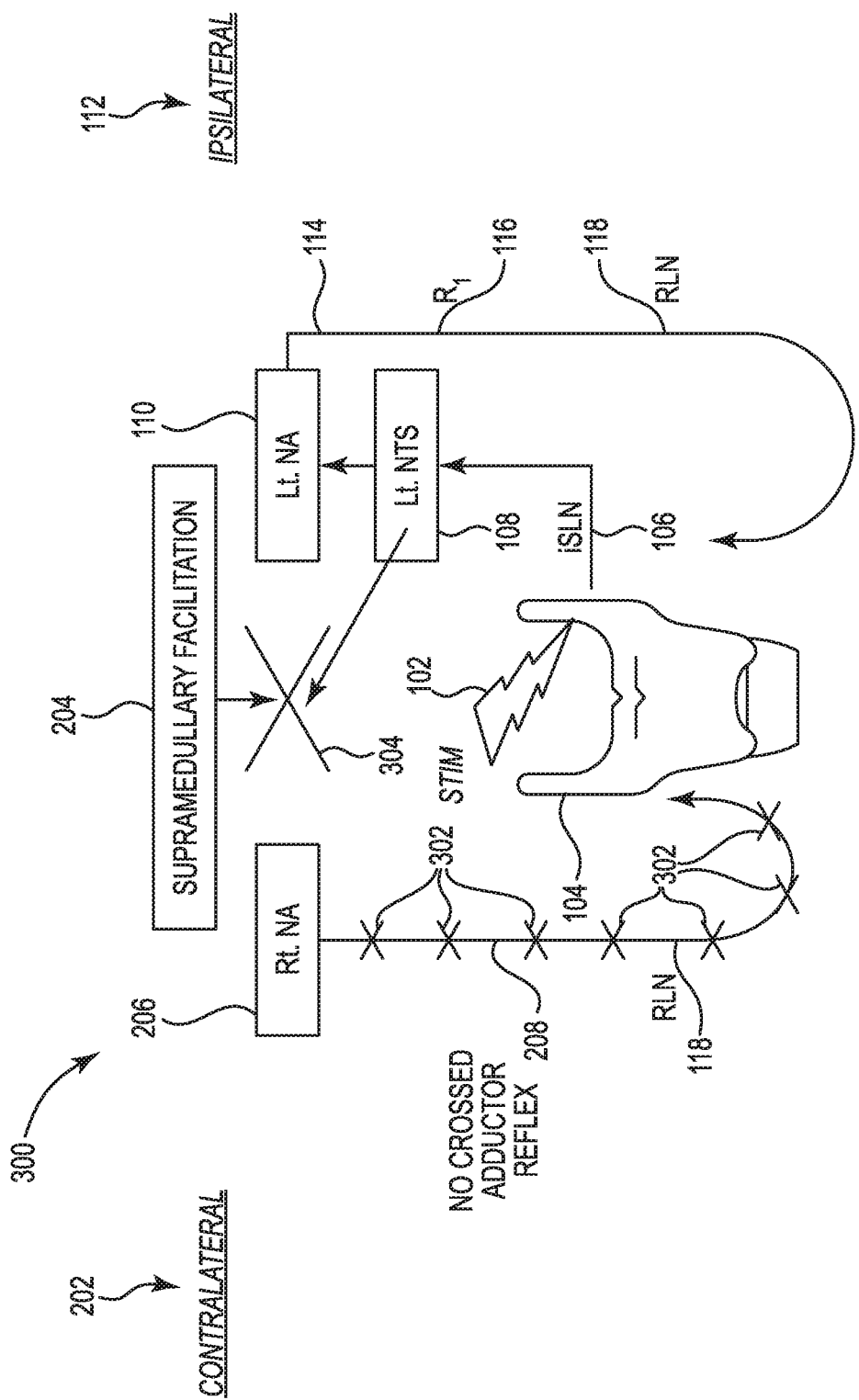
FIG. 3 is a diagram illustrating a normal response deep anesthesia ipsilateral reflex with no contralateral reflex according to one embodiment.

FIG. 3 is a diagram illustrating a normal response deep anesthesia ipsilateral reflex 300 with no contralateral reflex according to one embodiment. FIG. 3 is similar to FIG. 2, but the deep anesthesia results in the loss of the crossed adductor reflex 208, as represented by the "X" symbols 302 and 304.

Figure 4:
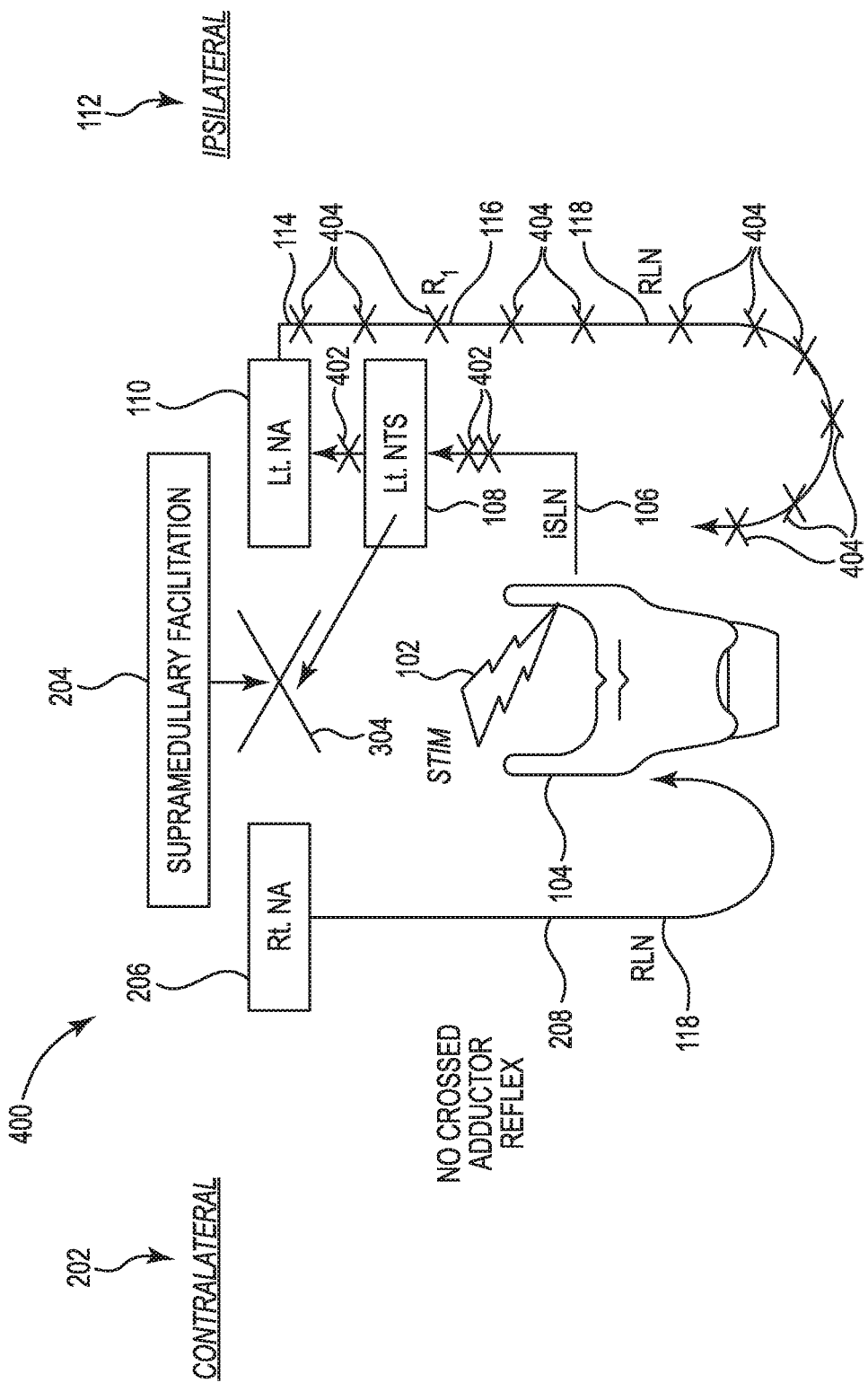
FIG. 4 is a diagram illustrating an ipsilateral loss of signal and a potential internal superior laryngeal nerve (iSLN) injury (alert surgeon) according to one embodiment.

FIG. 4 is a diagram illustrating an ipsilateral loss of signal and a potential internal superior laryngeal nerve (iSLN) injury (alert surgeon) situation 400 according to one embodiment. FIG. 4 is similar to FIG. 2, but the potential iSLN injury results in the loss of the sensory nerve signals that travel up the iSLN branch 106, as represented by the "X" symbols 402, and results in the loss of the ipsilateral reflex 112, as represented by the "X" symbols 404. The crossed adductor reflex 208 is also lost, as represented by the "X" symbol 304.

Figure 5:
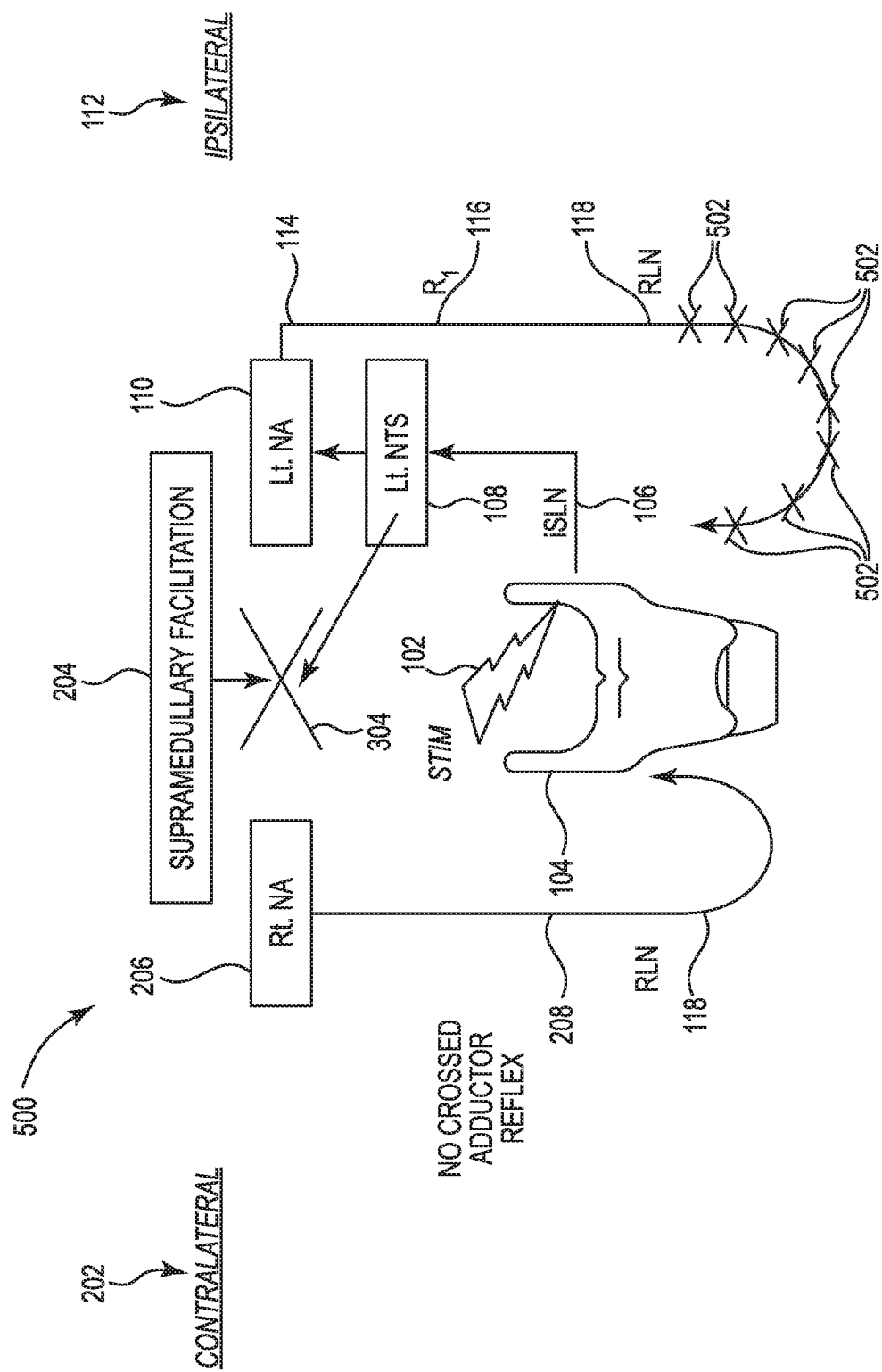
FIG. 5 is a diagram illustrating an ipsilateral loss of signal and a potential recurrent laryngeal nerve (RLN) injury (alert surgeon) according to one embodiment.

FIG. 5 is a diagram illustrating an ipsilateral loss of signal and a potential recurrent laryngeal nerve (RLN) injury (alert surgeon) situation 500 according to one embodiment. FIG. 5 is similar to FIG. 2, but the potential RLN injury results in the loss of the RLN 118 evoking muscle movement at the larynx 104, as represented by the "X" symbols 502. The crossed adductor reflex 208 is also lost, as represented by the "X" symbol 304.

Figure 6A:
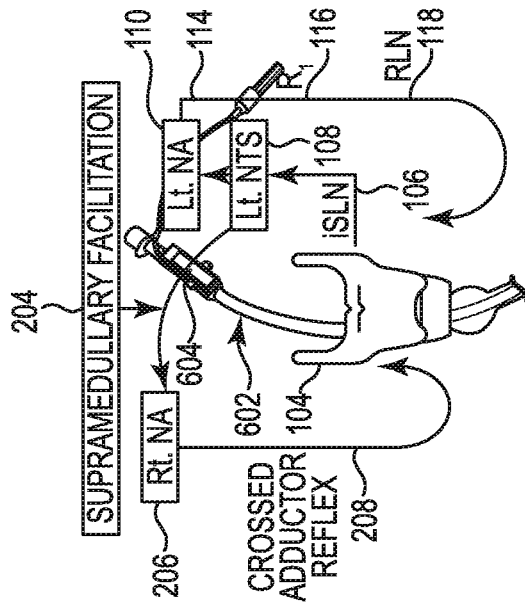
FIGS. 6A-6D are diagrams illustrating a system that detects depth of anesthesia and detects nerve injury to iSLN and RLN according to one embodiment.
Figure 6B:
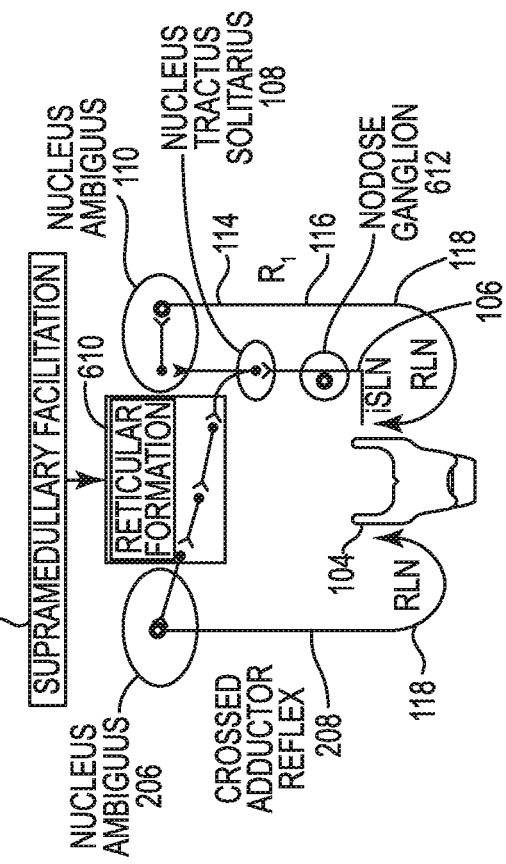
Figure 6C:
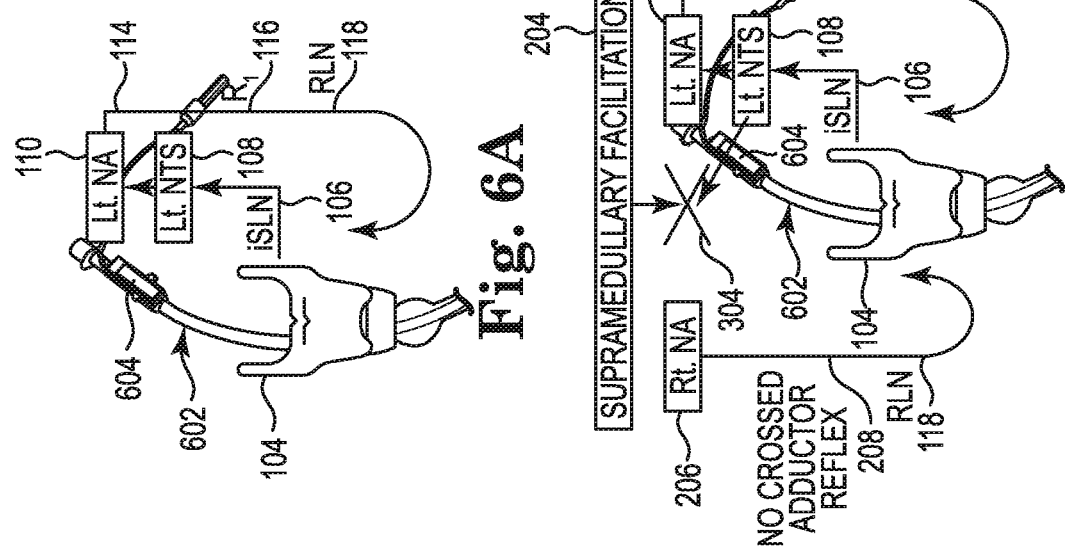
Figure 6D:

FIGS. 6A-6D are diagrams illustrating a system that detects depth of anesthesia and detects nerve injury to iSLN and RLN according to one embodiment. FIG. 6A is similar to FIG. 1, but includes an endotracheal tube apparatus 602 with a module 604 (described in further detail below) to provide the stimulation 102 (FIG. 1) at the larynx 104. The endotracheal tube apparatus 602 may be used to detect depth of anesthesia and detect nerve injury to iSLN and RLN. FIG. 6B is similar to FIG. 2 and shows a light anesthesia bilateral reflex, but includes endotracheal tube apparatus 602 with module 604 to provide the stimulation 102 (FIG. 2) at the larynx 104. FIG. 6C is similar to FIG. 3 and shows a deep anesthesia ipsilateral reflex with no contralateral reflex, but includes endotracheal tube apparatus 602 with module 604 to provide the stimulation 102 (FIG. 3) at the larynx 104. As shown in FIG. 6D, in response to stimulation being applied to larynx 104, sensory nerve signals travel up the iSLN branch 106 of the vagus nerve 114 to nodose ganglion 612, left nucleus tractus solitarius (Lt. NTS) 108, and left nucleus ambiguus (Lt. NA) 110, which evoke a reflex ($R_1$) 116 that travels down the vagus nerve 114 to the recurrent laryngeal nerve (RLN) 118, which evokes muscle movement at the larynx 104. In addition, supramedullary facilitation 204 and reticular formation 610 cause the right nucleus ambiguus (Rt. NA) 206 to evoke a crossed adductor reflex 208, which evokes muscle movement at the larynx 104.

Figure 7A:
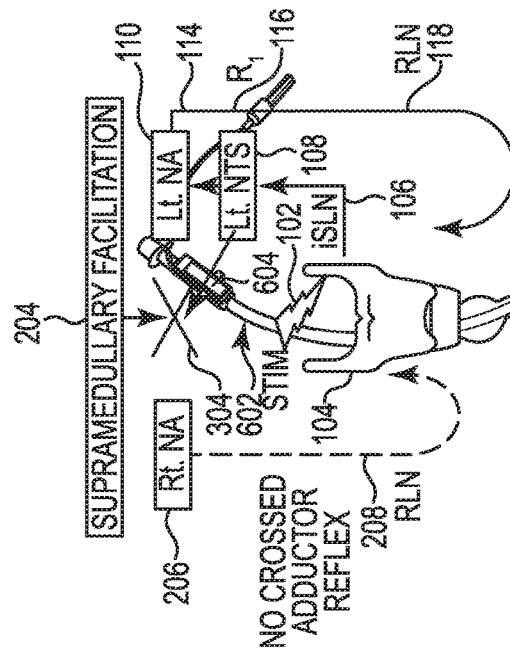
FIGS. 7A-7D are diagrams illustrating recording for light anesthesia and deep anesthesia, and iSLN injury and RLN injury according to one embodiment.
Figure 7B:
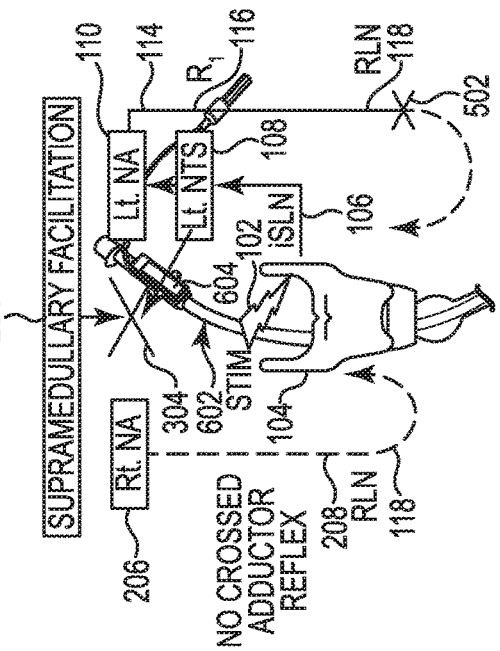
Figure 7C:
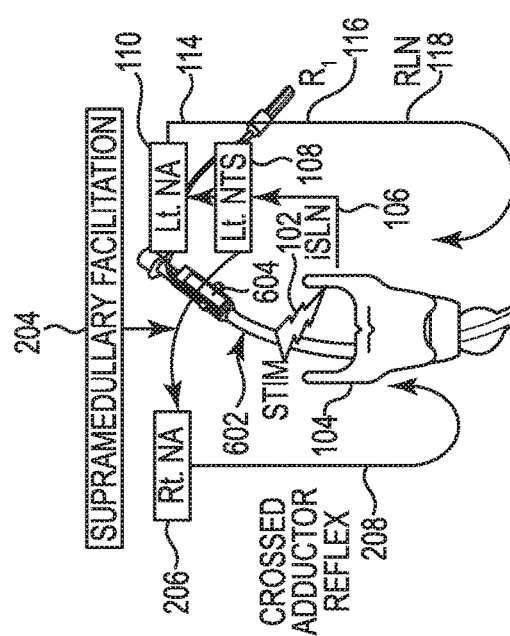
Figure 7D:
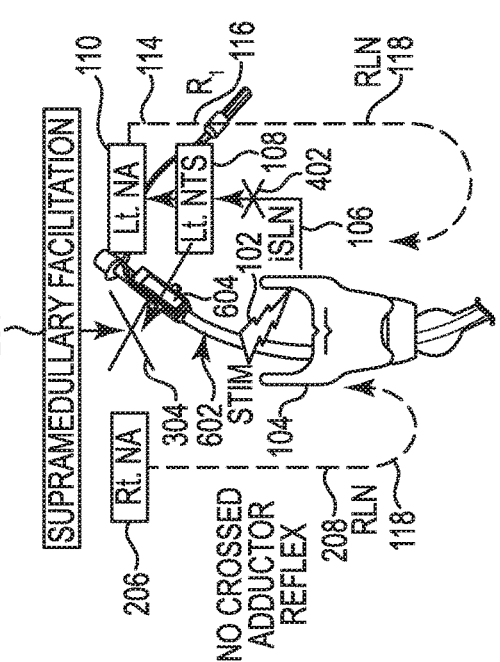

FIGS. 7A-7D are diagrams illustrating recording for light anesthesia and deep anesthesia, and iSLN injury and RLN injury according to one embodiment. FIG. 7A is similar to FIG. 2, but includes an endotracheal tube apparatus 602 with a module 604 to provide the stimulation 102 at the larynx 104 and identify the light anesthesia status. FIG. 7B is similar to FIG. 3, but includes endotracheal tube apparatus 602 with module 604 to provide the stimulation 102 at the larynx 104 and identify the deep anesthesia status. Note that the "X" symbols 302 in FIG. 3 are replaced in FIG. 7B with a dashed line. FIG. 7C is similar to FIG. 4, but includes endotracheal tube apparatus 602 with module 604 to provide the stimulation 102 at the larynx 104, identify the iSLN injury, and alert the surgeon. Note that the loss of the crossed adductor reflex 208 is represented in FIG. 7C with a dashed line, and the "X" symbols 404 in FIG. 4 are replaced in FIG. 7C with a dashed line. FIG. 7D is similar to FIG. 5, but includes endotracheal tube apparatus 602 with module 604 to provide the stimulation 102 at the larynx 104, identify the RLN injury, and alert the surgeon. Note that the loss of the crossed adductor reflex 208 is represented in FIG. 7D with a dashed line, and some of the "X" symbols 502 in FIG. 5 are replaced in FIG. 7D with a dashed line.

Figure 8B:
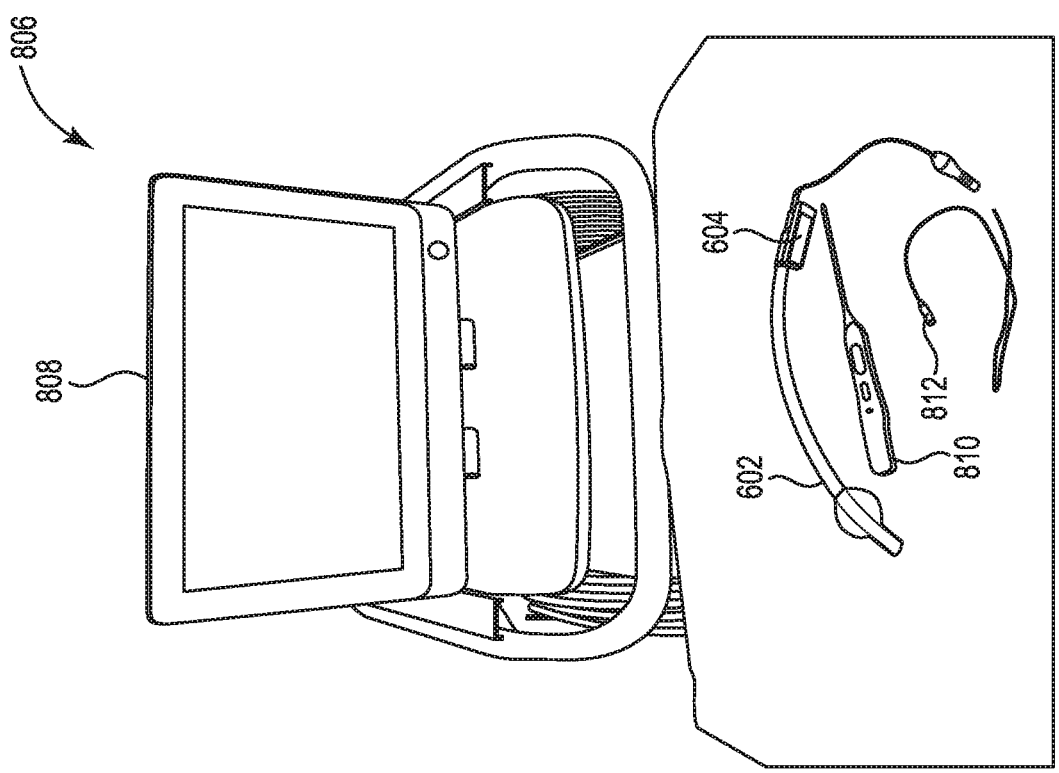
FIGS. 8A-8B illustrate a conventional nerve integrity monitoring system (FIG. 8A) with numerous wires compared to one embodiment of the present disclosure (FIG. 8B) with simplified connectivity.
Figure 8A:
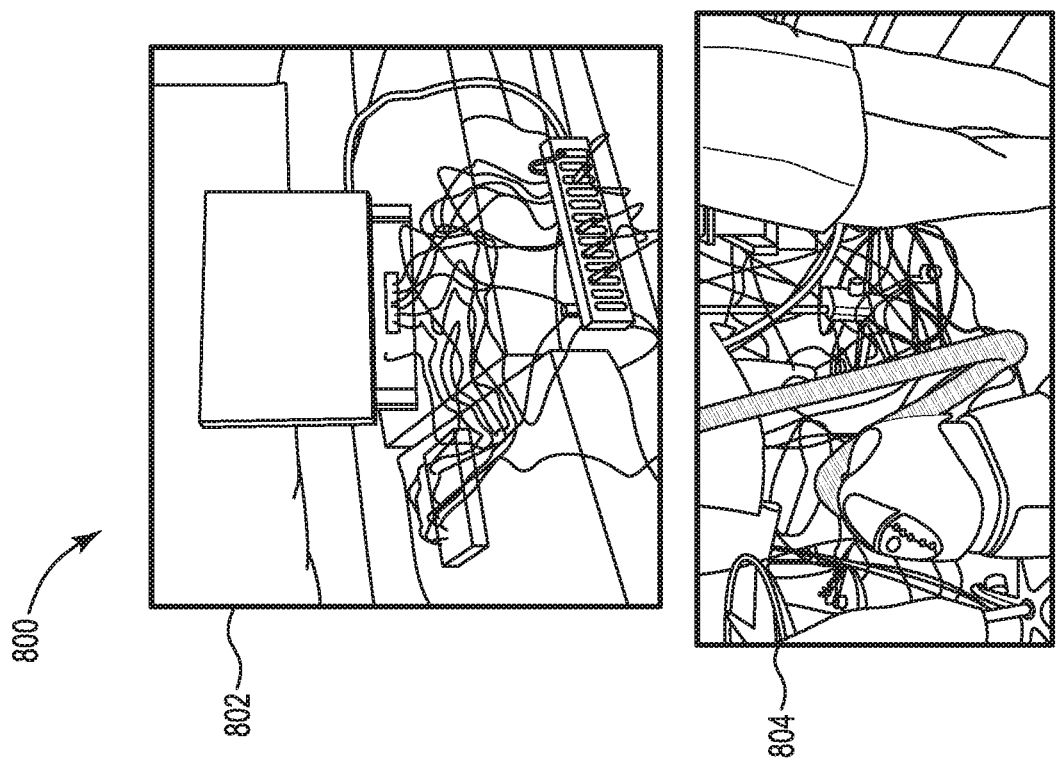

FIG. 8A illustrates a conventional nerve integrity monitoring system 800 with numerous wires. As shown at 802, the system 800 includes numerous wires above the operating room (OR) table, and as shown at 804, the system 800 includes numerous wires below the OR table. In contrast, FIG. 8B illustrates a nerve integrity monitoring system 806 with simplified connectivity according to one embodiment of the present disclosure. Nerve integrity monitoring system 806 includes nerve integrity monitor apparatus 808, probe 810, electrode 812, and endotracheal tube apparatus 602 with module 604.

Figure 9A:
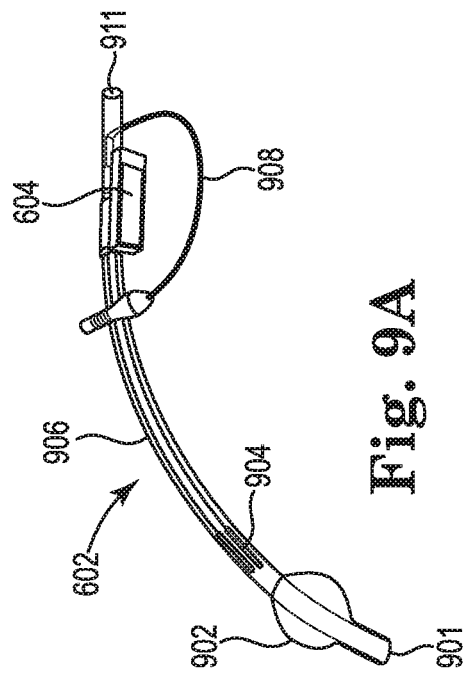
FIGS. 9A-9E illustrate the integration of an EMG tube and automatic periodic stimulation (APS) to evoke and record a laryngeal reflex according to one embodiment.
Figure 9B:
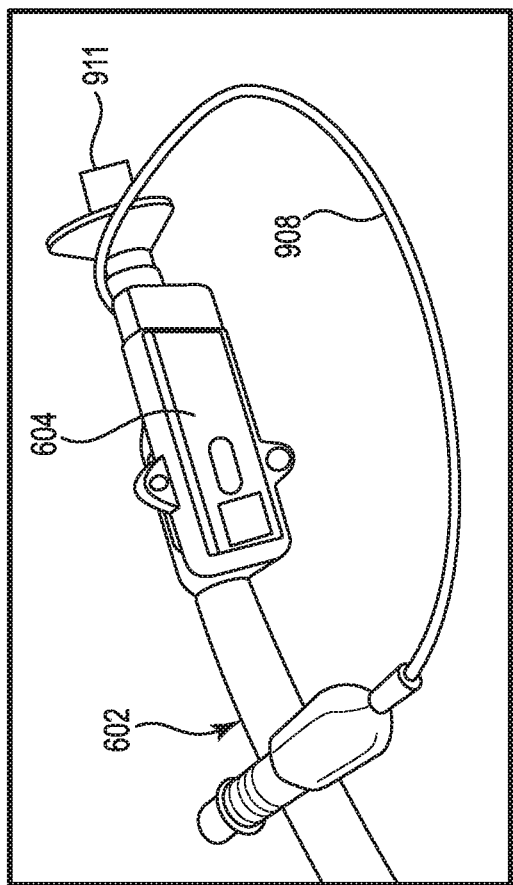
Figure 9C:
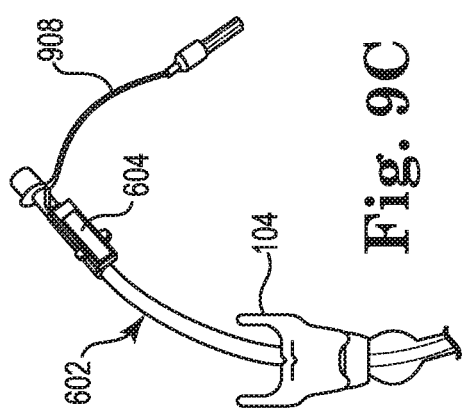
Figure 9D:
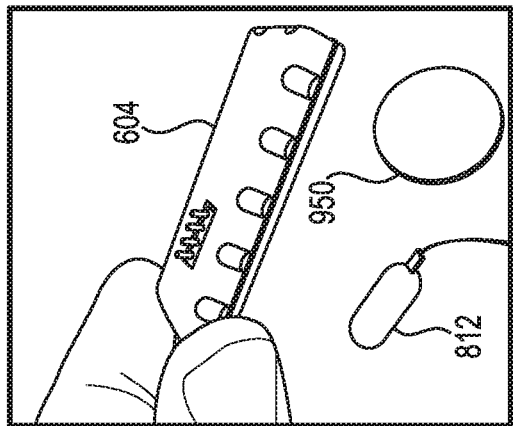
Figure 9E:
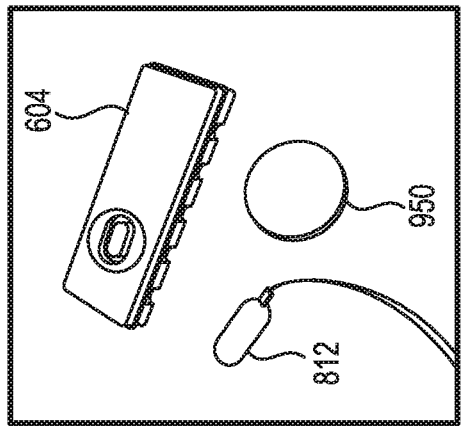

FIGS. 9A-9E illustrate the integration of an EMG tube and automatic periodic stimulation (APS) to evoke and record a laryngeal reflex according to one embodiment. FIG. 9A shows endotracheal tube apparatus 602, which includes module 604 positioned near a proximal end 911 of the apparatus 602 and a balloon cuff 902 positioned near a distal end 901 of the apparatus 602. The endotracheal tube apparatus 602 further includes electrodes 904, conductive traces 906, and cuff inflating conduit 908. FIG. 9B shows a close-up view of the proximal end 911 of the endotracheal tube apparatus 602, including the module 604. FIG. 9C shows the endotracheal tube apparatus 602 positioned in a larynx 104. FIG. 9D shows a view of a bottom side of the module 604. FIG. 9D also shows an electrode 812, and a dime 950 positioned near the module 604 (to illustrate the size of one embodiment of the module 604). FIG. 9E shows a view of a top side of the module 604 positioned next to the electrode 812 and the dime 950.

Figure 10:
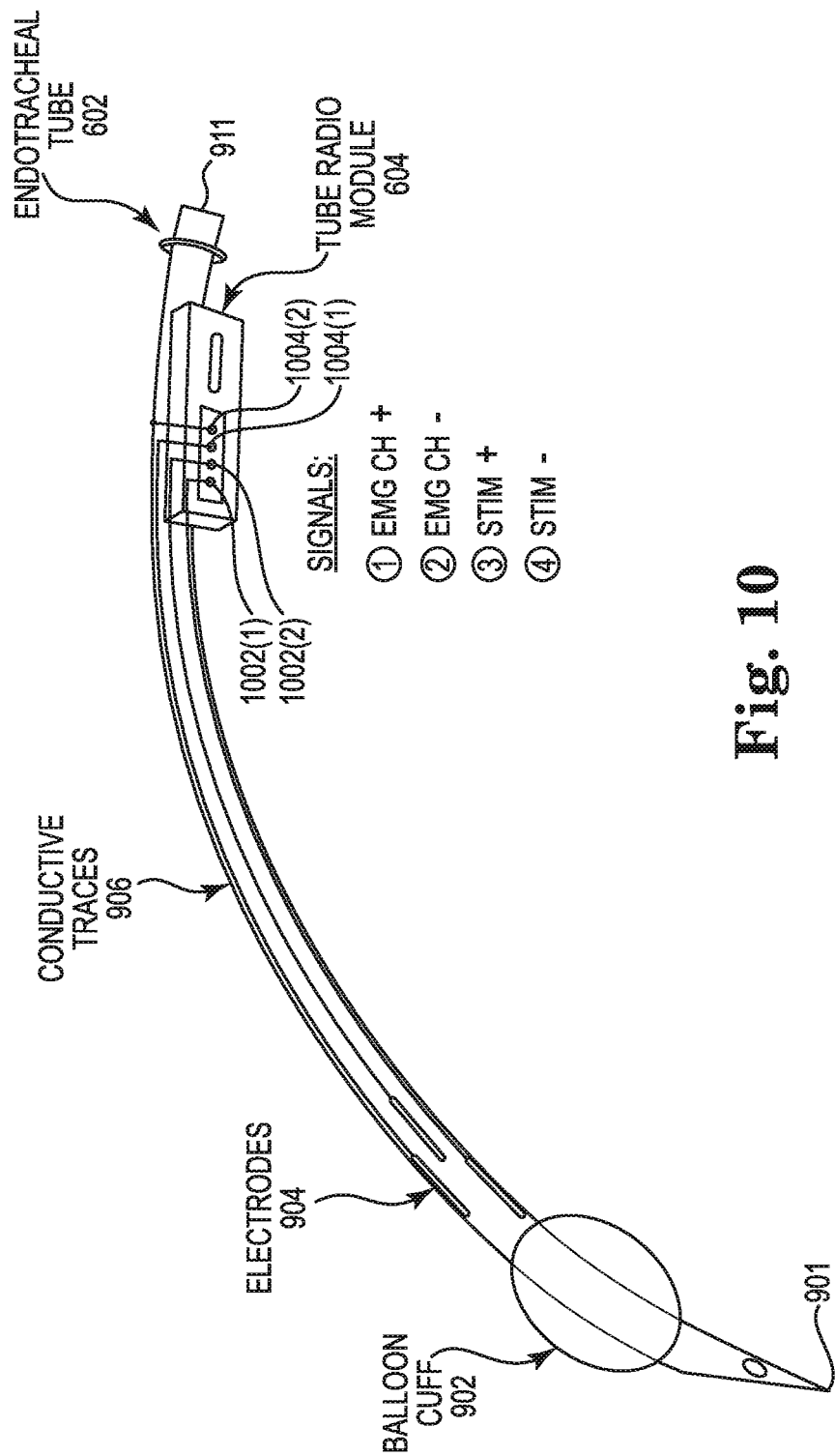
FIG. 10 is a diagram illustrating an EMG endotracheal tube with an integrated APS stimulator and laryngeal twitch detector according to one embodiment.

FIG. 10 is a diagram illustrating an EMG endotracheal tube apparatus 602 with an integrated APS stimulator and laryngeal twitch detector according to one embodiment. As shown in FIG. 10, the module 604 includes two EMG inputs 1002(1) (i.e., EMG CH+) and 1002(2) (i.e., EMG CH−) (collectively referred to as EMG inputs 1002), and two stimulation outputs 1004(1) (i.e., STIM+) and 1004(2) (i.e., STIM−) (collectively referred to as stimulation outputs 1004). As shown in FIG. 10, each of the inputs 1002 and outputs 1004 is connected to a respective one of the conductive traces 906, which are each connected to a respective one of the electrodes 904. The module 604 includes an accelerometer 1130 (FIG. 11) to detect vibration from a laryngeal twitch.

Figure 11:
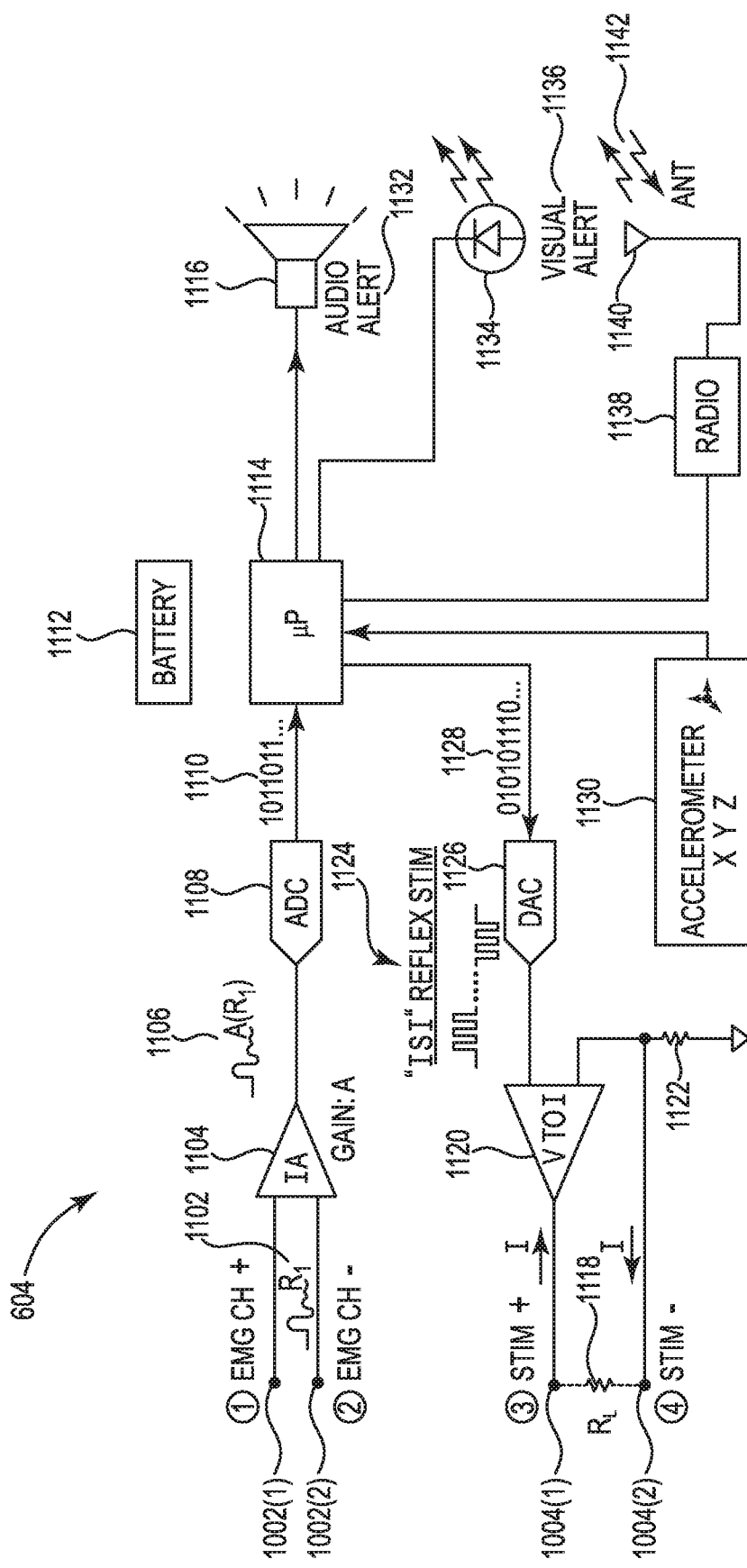
FIG. 11 is a block diagram illustrating a tube radio module according to one embodiment.

FIG. 11 is a block diagram illustrating a tube radio module 604 according to one embodiment. Module 604 includes instrumental amplifier (IA) 1104, analog to digital converter (ADC) 1108, battery 1112, processor (e.g., microprocessor or μP) 1114, speaker 1116, resistor 1118, voltage to current (V to I) converter 1120, resistor 1122, digital to analog converter (DAC) 1126, accelerometer 1130, light emitting element 1134, radio 1138, and antenna 1140.

Processor 1114 generates digital stimulation signals 1128, which are converted by digital to analog converter 1126 into analog stimulation signals 1124 (e.g., analog reflex stimulation pulses having a particular inter stimulus interval (ISI)). Voltage to current converter 1120 converts the analog stimulation signals 1124 from voltage signals to current signals, which are output from the module 604 via outputs 1004(1) and 1004(2).

Module 604 receives EMG signals ($R_1$) 1102 from the inputs 1002(1) and 1002(2). The instrumental amplifier 1104, which has a gain of A, receives and amplifies the EMG signals 1102, and outputs amplified signal ($A(R_1)$) 1106 to analog to digital converter 1108. Analog to digital converter 1108 converts the analog signal 1106 to a corresponding digital signal 1110 for processing by processor 1114.

Accelerometer 1130 functions as a laryngeal twitch detector and outputs 3-axis (e.g., X, Y, and Z) accelerometer data to processor 1114 for processing. Processor 1114 outputs a signal to speaker 1116 to provide an audio alert 1132. Processor 1114 outputs a signal to light emitting element 1134 to provide a visual alert 1136. Processor 1114 is also coupled to a radio 1138 and antenna 1140 for wireless communications 1142 (e.g., to wirelessly communicate with a probe 810 or console 808).

Figure 12:
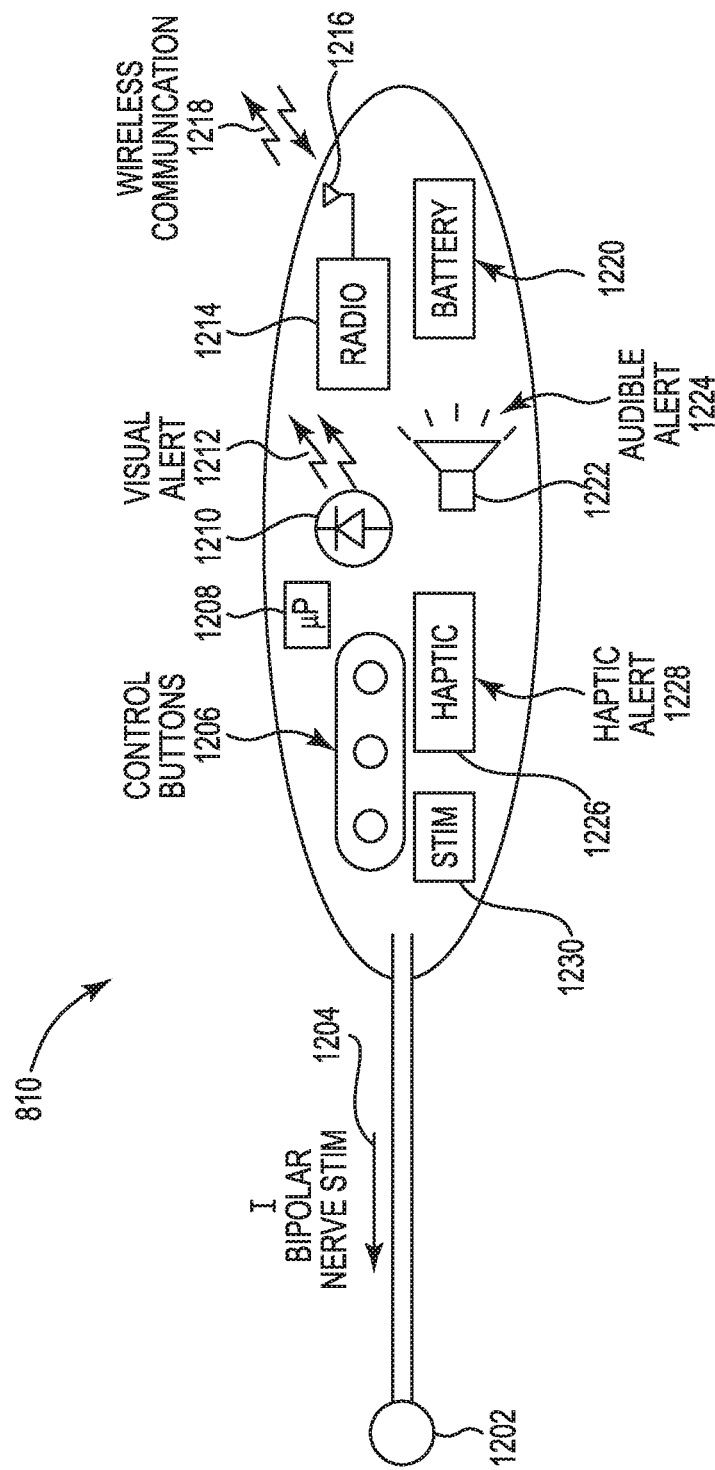
FIG. 12 is a diagram illustrating a nerve probe with surgeon alerts according to one embodiment.

FIG. 12 is a diagram illustrating a nerve probe 810 with surgeon alerts according to one embodiment. Nerve probe 810 includes a probe tip 1202 to deliver bipolar nerve stimulation signals 1204. In other embodiments, nerve stimulation signals 1204 may be monopolar nerve stimulation signals. Nerve probe 810 includes control buttons 1206; processor (e.g., microprocessor or μP) 1208; light emitting element 1210 to provide a visual alert 1212; radio 1214 and antenna 1216 for wireless communications 1218 with an endotracheal tube (e.g., an EMG-APS tube); battery 1220; speaker 1222 to provide an audible alert 1224; haptic element 1226 to provide a haptic alert 1228; and stimulation element 1230 to generate the stimulation signals 1204. Nerve probe 810 may vibrate, blink, and beep to alert a surgeon.

Figure 13A:
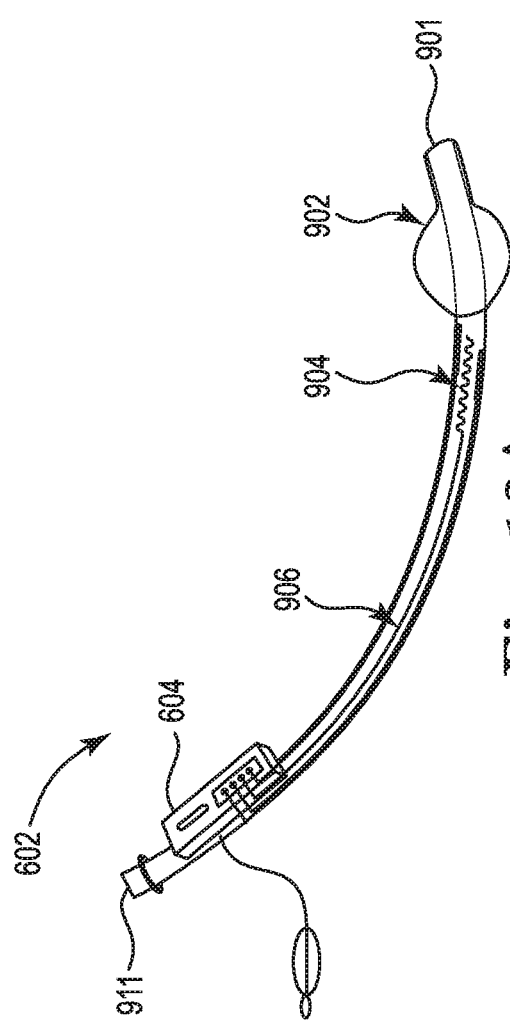
FIG. 13A is a diagram illustrating an EMG endotracheal tube configured to perform reflex stimulation according to one embodiment.
Figure 13B:
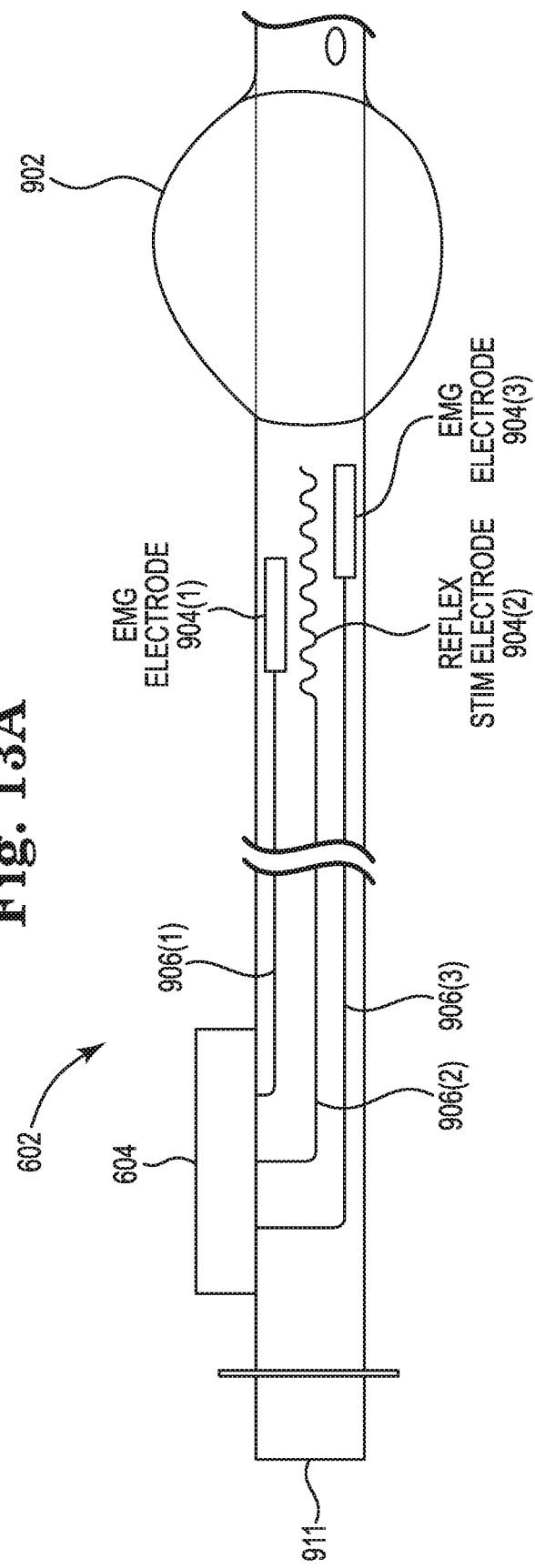
FIG. 13B is a diagram illustrating a zoomed-in view of a portion of the EMG endotracheal tube shown in FIG. 13A according to one embodiment.

FIG. 13A is a diagram illustrating an EMG endotracheal tube 602 configured to perform reflex stimulation according to one embodiment. FIG. 13B is a diagram illustrating a zoomed-in view of a portion of the EMG endotracheal tube 602 shown in FIG. 13A according to one embodiment. Electrodes 904 of endotracheal tube 602 includes EMG electrode 904(1), reflex stimulation electrode 904(2), and EMG electrode 904(3). Conductive traces 906 include conductive traces 906(1), 906(2), and 906(3), which are respectively connected to EMG electrode 904(1), reflex stimulation electrode 904(2), and EMG electrode 904(3). Conductive traces 906 are also connected to module 604. As shown in FIG. 13B, the EMG electrodes 904(1) and 904(3) are positioned on an exterior surface of the tube 602, and are laterally and longitudinally offset from each other. The reflex stimulation electrode 904(2) has a sinusoidal shape and is positioned between the EMG electrodes 904(1) and 904(3) on the exterior surface of the tube 602. In the illustrated embodiment, the EMG electrodes 904(1) and 904(3) and the reflex stimulation electrode 904(2) are positioned on the same side of the tube 602. In another embodiment, tube 602 includes an EMG electrode 904(1) on one side of the tube 602, and a stimulation electrode 904(2) on an opposite side of the tube. Balloon cuff 902 is positioned longitudinally distal to the electrodes 904(1)-904(3) and is positioned near a distal end 901 of the apparatus 602.

Some embodiments replace the need for directly contacting the motor nerve branches and motor nerve trunks with a probe or electrode, which results in a safer procedure. The nerve tissue is not subjected to risk of injury from direct contact or dissection that may compromise the blood supply and microvasculature. Moreover, embodiments disclosed herein provide economic value to the user by reducing user error, setup time, and procedure time.

Some embodiments are directed to an EMG tube 602 with at least four conductive electrodes 904, at least two of which may stimulate tissue in a nerve monitoring application (e.g., stimulating to evoke a laryngeal reflex). Some embodiments provide one or more of the following capabilities: (1) preoperatively quantify a patient's vocal cord function before incision and dissection; (2) post-operatively quantify a patient's vocal cord function after dissection and after surgical wound closure; (3) detect injury to the recurrent laryngeal nerve (RLN) and the internal superior laryngeal nerve (iSLN); and (4) determine the depth of patient anesthesia by two methods: (a) A train-of-four stimulus is delivered to the laryngeal mucosa using the stimulation electrodes of the tube 602; and the number of corresponding reflex twitches is measured to determine the depth of anesthesia of the patient; and (b) detecting the presence or absence of the contralateral reflex.

Some embodiments provide one or more of the following additional capabilities: (1) confirmation of proper tube placement; (2) confirmation of nerve pathways without placing an electrode on the nerve; and (3) providing a nerve monitor without a console.

Some embodiments are directed to an endotracheal tube 602 that integrates a wireless tube radio module 604 and a wireless automatic periodic stimulation (APS) electrode 904, providing the capability of monitoring without the typical nerve integrity monitor (NIM) console base station. Stimulation (e.g., APS) may be incorporated into an EMG tube radio module 604 to elicit a reflex for continuous intraoperative nerve monitoring (CIONM). Some embodiments may act as a standalone nerve monitoring system that alerts the surgeon of degraded nerve function using audible, visual or haptic alerts that originate from either the tube 602 itself or a stimulation instrument. Some embodiments provide a means to monitor the integrity of the neural pathways of the larynx without directly stimulating the nerve tissue. Some embodiments remove barriers to customer adoption by eliminating the requirement to dissect the vagus nerve within the carotid sheath and eliminating the need for wrap around cuff electrodes. Some embodiments exploit the laryngeal reflex, and involve automatic periodic stimulation of the laryngeal mucosa, recording laryngeal electromyography, and recording laryngeal twitch mechanomyography.

Currently, to use CIONM for Thyroid Surgery, there is a need to dissect the vagus nerve in order to place an APS stimulated cuff electrode, which is a significant barrier to market adoption. Some embodiments disclosed herein reduce the difficulty in performing continuous monitoring of the RLN by using noninvasive methods for periodic stimulation of the RLN, while reducing the signal variation caused by EMG tube position. Nerve reflex arcs can be exploited to monitor both the sensory and motor nerves at risk in Thyroidectomy. These nerve reflexes may be used to evoke responses without placing a cuff electrode directly on the nerve.

Some embodiments disclosed herein are directed to continuously monitoring the vagus/RLN without adding time and difficulty to the surgery. Some embodiments involve evoked potential monitoring for the sensory nerves of the internal branch of the superior laryngeal nerve (IBSLN), RLN, and glossopharyngeal nerves. Some embodiments involve the exploitation of reflex arcs such as pharyngeal (gag) reflex, pharyngoglottal closure reflex, or Hoffman reflex (H-wave and F-wave), and evoke these reflexes using an EMG tube 602 to provide electrical stimulation. Regarding the pharyngeal (gag) reflex, a normal neural reflex is elicited by touching the soft palate or posterior pharynx, and the response is a symmetric elevation of the palate, a retraction of the tongue, and a contraction of the pharyngeal muscles. It may be used as a test of the integrity of the vagus and glossopharyngeal nerves. The H-reflex (or Hoffman reflex) is a reflectory reaction of muscles after electrical stimulation of sensory fibers.

In a reflex arc, a series of physiological steps occur very rapidly to produce a reflex. Generally, a sensory receptor receives an environmental stimulus, in this case from objects reaching nerves in the back of the throat, and sends a message via an afferent nerve to the central nervous system (CNS). The CNS receives this message and sends an appropriate response via an efferent nerve (also known as a motor neuron) to effector cells located in the same initial area that can then carry out the appropriate response.

In the case of the pharyngeal reflex, the sensory limb is mediated predominantly by CN IX (glossopharyngeal nerve), and the motor limb by CN X (vagus nerve). The gag reflex involves a brisk and brief elevation of the soft palate and bilateral contraction of pharyngeal muscles evoked by touching the posterior pharyngeal wall. Touching the soft palate can lead to a similar reflex response. However, in that case, the sensory limb of the reflex is the CN V (trigeminal nerve).

Closely related to the gag reflex, in which food or other foreign substances are forced back out of the pharynx, swallowing generally pushes food through the digestive system into the stomach. This reflex in particular functions as a protective system for the upper respiratory tract as it not only forces the glottis to close, thereby preventing any substances getting into the airways, but also clears the pharynx of any residual substances by a swallow. This particular reflex is one of several aero digestive reflexes such as the reflexive pharyngeal swallow, the pharyngoglottal closure reflex, in which no swallowing occurs yet the glottis still closes.

One embodiment uses an EMG tube 602 and nerve integrity monitor (NIM) 808 for monitoring the vocal folds, and electrically evoking a reflex arc involving the vagus nerve and recurrent laryngeal nerve. Differing combinations of the electrodes 904 may be used for neurogenic stimulation and recording corticospinal and central motor pathways. Differing combinations of APS for single and reflex/facilitation repetitive stimulation of the following 7-step method may be used:

(1) Connect the electrodes 904 of the EMG tube 602 to the NIM Patient Interface as indicated in Table I below.

(2) Set the stimulator to 1 mA. Observe the NIM 808 for any signals captured with a significant latency indicating a reflex arc is evoked.

(3) Increase the stimulus to 3 mA. Observe the NIM 808 for any signals captured with a significant latency indicating a reflex arc is evoked.

(4) Increase the stimulus to 10 mA. Observe the NIM 808 for any signals captured with a significant latency indicating a reflex arc is evoked.

(5) Increase the stimulus to 20 mA. Observe the NIM 808 for any signals captured with a significant latency indicating a reflex arc is evoked.

(6) Increase the stimulus to 30 mA. Observe the NIM 808 for any signals captured with a significant latency indicating a reflex arc is evoked.

(7) Repeat for each electrode combination in Table I.

TABLE I

| | | | | Stim Setting | | | | |
|---|---|---|---|---|---|---|---|---|
| Stim+ | Stim− | Rec+ | Rec− | 1 mA | 3 mA | 10 mA | 20 mA | 30 mA |
| Red | Blu | RedWht | BluWht | | | | | |
| Red | BluWht | Blu | RedWht | | | | | |
| Red | RedWht | Blu | BluWht | | | | | |
| Blu | BluWht | Red | RedWht | | | | | |
| Blu | RedWht | Red | BluWht | | | | | |
| RedWht | BluWht | Red | Blu | | | | | |

Stimulation and monitoring may also be performed by placing paired needle or surface electrodes in or on the Vocalis (or musculature adjacent) vocal folds or Cricothyroid muscle for recording EMG responses, systematically probing the larynx with a long shaft stimulation probe 810, and capturing any evoked potentials on a NIM 808. Note that any long latency responses may be a reflex potential. Based on the captured information, areas of the larynx that may have evoked the pharyngoglottal closure reflex or the pharyngeal (gag) reflex may be identified.

Some embodiments use an EMG tube 602 and a NIM 808 to provide stimulation and recording, monitoring and evoking glottic closure reflex through activation of neurogenic corticospinal and central motor pathways with multi-pulse stimulation train sequences used for motor evoked potentials (MEPs). This may be performed by stimulating the EMG tube electrodes 904 with multiple pulse sequences causing a reflex closure of VF. Normal MEP parameters may be used (e.g., 100 us pulse, 2-5 ms ISI, 3-5 pulses, + and − polarity).

The setting of 1 or 2 mA to >20 mA may be used. The method may involve stimulating pulses at distal glottic sensory nerve receptors. These sensory nerve signals travel up VN and are summated evoking a reflex at the brain stem. The reflex travels back down VN to RL evoking muscle movement at VF. Evoked reflex EMG signals may be recorded with the NIM device 808.

Some embodiments use an EMG tube 602 and a NIM 808 to provide stimulation and recording, monitoring and evoking glottic closure reflex, and may use stimulation facilitation methods (example: double train stimulation, Tetanic stimulation) to improve effectiveness (amplitude and consistency) of evoking reflex responses activation of neurogenic corticospinal and central motor pathways with stimulation train sequences used for motor evoked potentials (MEPs). Facilitation by double train would consist of train stimulation repeated at interval <1 Second followed by recording the reflex. Facilitation by Tetanic stimulation would consist of pre-stimulation of a nerve (Example Ulnar nerve) at 30-60 Hz for 1-10 Seconds followed by Reflex stimulation and recording.

Some embodiments are directed to an evoked potential monitoring system that uses a NIM device 808 that provides multi-pulse, multiphasic automatic stimulation, which may be combined with APS. Many different electrode types may be used (e.g., conductive electrode, surface electrode, needle electrode, etc.). The electrodes 904 may do the stimulation, recording, and conveying an alerting signal. The electrodes 904, or mechanical transducers, may do the stimulation, and the hand-held probe 810 may be configured for neurogenic recording. The hand-held probe 810 may be configured for stimulation, recording, and alerting signal. Some embodiments may include wireless functionality for stimulation, recording, monitoring, synchronizing, and alerting. Some embodiments may use one or more of a wireless NIM 808, wireless electrodes, a wireless stimulator or stimulation probe 810, a wireless EMG tube 602, and a wireless patient hub. The wireless EMG tube 602 may communicate with various devices, including a NIM 808, a mobile phone, a mini re-sterilizable remote control device in the operating room, a probe 810 that has a display on it, as well as other devices. Some embodiments may use various wireless systems and methods, or other systems and methods, such as those disclosed in U.S. Patent Pub. Nos. 2016-0038073, 2016-0038074, 2016-0038072, 2016-0287112, 2016-0287861 and 2017-0007146, which are hereby incorporated by reference herein. Some embodiments may involve a probe 810, which may be synchronized with APS and alerts. The system may have tactile feedback in a probe 810 monitoring a nerve.

The NIM 808 used in some embodiments may include one or more of the following features: a multi-app modular system; wireless printing and other wireless features; EMR integration; remote monitoring; anatomical picture annotation; remote support and updates, including audio and video conferencing capabilities; detachable display; compatible with Nav/Peak platforms; a simple to use GUI; automated waveform interpretation; and network connectivity. In some embodiments, the system may further include one or more of the following features: a setup/training wizard; a loss-of-signal diagnostic wizard; a flex face electrode template; a wireless patient hub; and wireless stimulating hemostats. Some embodiments of the present disclosure may be used for one or more of the following: acoustic nerve monitoring; somatosensory evoked potentials; occularmotor EMG; visually evoked potentials; olfactory nerve monitoring; spinal accessory nerve monitoring; colorectal striated EMG; colorectal smooth EMG; and colorectal bladder pressure.

Some embodiments involve stimulation using an electrode 904, an electrode 904 on a tube 602, and APS stimulation on a tube 602, and mechanically eliciting a response, combined with one or more of the following: monitoring a bioelectric signal; monitoring a bioelectric signal that is also mechanically elicited; monitoring amplitude or latency of a signal; monitoring an EMG signal; providing an alert on change of signal; providing an alert that is audio, visual, and/or tactile vibration; providing therapeutic stimulation based monitoring of a signal; evoked potential monitoring system that is configured to both stimulate and record to the same electrodes 904; monitoring a nerve with APS single or multi-pulse stimulation and recording, which may use many different electrode types besides the cuff used throughout the body, (e.g., conductive electrode, wire, surface electrode, needle electrode, etc.), and the electrode 904 could do the stimulation, recording and self-contained conveying of an alerting signal; wireless application that may add APS stimulation and recording, and may also add stimulation, recording, monitoring, synchronizing, and alerting; and probe application synchronized with APS and alerts, and may have tactile feedback in a probe 810 monitoring a nerve.

The following are some characteristics of evoked nerve action potential thresholds of various electrical nerve stimulation tips and stimulation algorithms according to one embodiment: (1) polarity may not matter with tips spaced at 1-10 mm oriented along the length of a nerve; (2) and polarity may be important with cathode on nerve with tips spaced 2-10 mm oriented perpendicular to the nerve; (3) regarding stimulation polarity switching, an alternate polarity separated blanking period may have a lower threshold and may not be affected by orientation to the nerve, and 100-200 uS may be used (responses may be elicited at lower current down to 0.5 mA at 200 uS), and a spacing of 1.3-2.0 mm may be used.

Some embodiments are directed to simplifying continuous intraoperative nerve monitoring (CIONM). A battery powered stimulator may be used to evoke vagus nerve action potentials, and produce a stable level of responses while the tissue is being manipulated. The CIONM stimulator may provide APS stimulation or Train-Of-Four (TOF) stimulation. The stimulator may be synchronized with the NIM 808. Various methods may be used to evoke reflexes for CIONM, including stimulating and recording from an EMG tube 602, which may involve stimulating at, above and/or below the level of the vocal folds and recording from the EMG tube 602. In one embodiment, the stimulation may be at >10 mA, and recording may be performed across the tube 602. In another embodiment, the stimulation may be provided below the vocal folds (e.g., >20 mA posterior). In yet another embodiment, the stimulation may be provided above the vocal folds (e.g., >20 mA anterior).

Some embodiments are directed to systems and methods of stimulation and monitoring nerves contained in the same electrode or probe. This can be applied to a nerve stimulation and monitoring endotracheal tube electrode 904 monitoring the nerves of the larynx or more broadly applied to other types of electrodes (e.g., needle, surface, wire, cuffed, probe, pledget, ball, etc.) that are used for both stimulation and recording and to assess neurological function.

For the EMG tube application, neurophysiological assessment can be used to aid in optimizing monitoring for neuro protection. Separate reflexes from the brain stem motor nucleus, supra-medullary facilitation and crossed adductor reflex pathway can be differentiated. Inhalational anesthetic agents effecting motor nucleus EMG less than faciliatory reflexes can be identified. A stimulation technique of single pulses and a volley of pulses reflex stimulation can differentiate motor nucleus reflex from faciliatory reflex.

An electrode 904 (with stimulation and recording in the same device) may be used to assess neurological function, optimized monitoring or protection features: (1) endotracheal (ET) tube 602 system stimulates/detects potential depth of anesthesia by inhibited EMG from APS reflex stimulation; (2) ET tube 602 can be optimally positioned with a technique using APS with a reflex stimulation profile until EMG detected is maximized and balanced; (3) ET tube electrode 904 can stimulate/detect by using a mechanical or electrical means to evoke a nerve response and mechanical or electrical means to record a response; (4) APS with single and a reflex stimulation profile can be monitored and used to trend, alert, alarm neuro pathways, brain stem, and motor cortex evoked faciliatory potentials.

CIONM stimulation parameters for APS of single and reflex stimulation profiles pulse methods include rate, polarity, width, interval delay, pulses, interphase delay, and repetition rate, i.e.: Stim Rate 1, 2, 4, 7, 10, 20 Hz, Typical 4 Hz, Pulses Square Wave: Monophasic (+ or −), Biphasic (−+) or (+−), Alternating Polarity; Pulses 50, 100, 250, 500, and 1000 uS, Typical 100 us microseconds; ISI (Inter stimulus interval) delay between pulses, i.e. 1-9 mS typical 2, 3 or 4 milliseconds; Pulse repetitions, i.e. a group of 1-8 positive; Interphase delay 0, 50, 100, 500, 1000 uS. Repetition Rate 1, 2, 4, . . . 120 pulses/minute, Typical 1 Hz.

Figure 14:
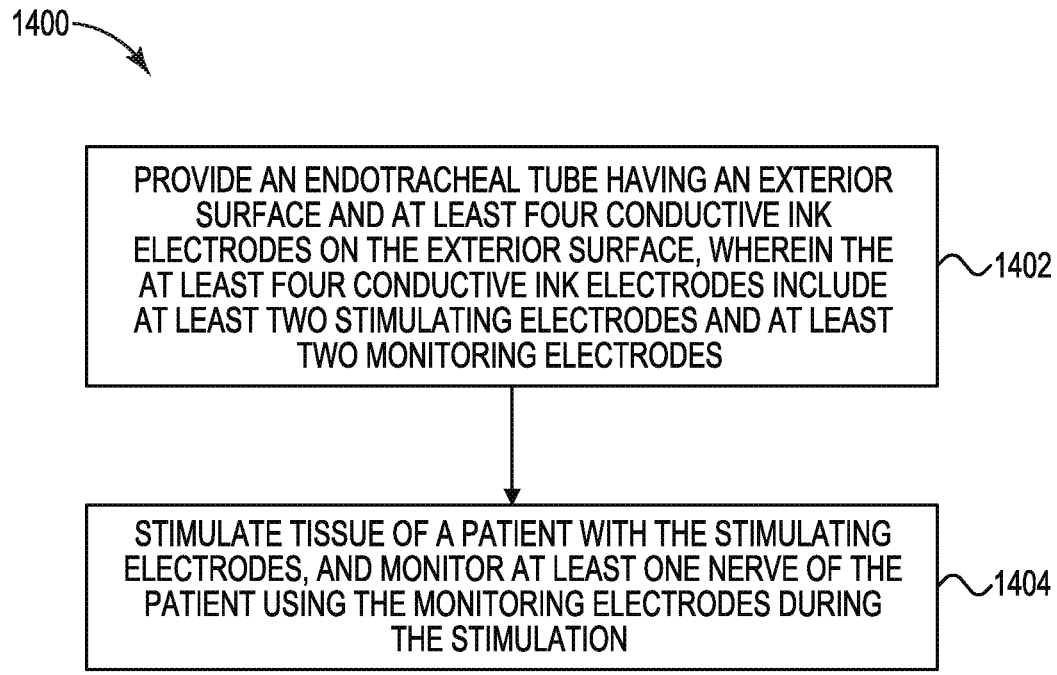
FIG. 14 is a flow diagram illustrating a method of stimulating and monitoring with an endotracheal tube according to one embodiment.

One embodiment is directed to a method of stimulating and monitoring with an endotracheal tube. FIG. 14 is a flow diagram illustrating a method 1400 of stimulating and monitoring with an endotracheal tube according to one embodiment. At 1402, the method 1400 includes providing an endotracheal tube having an exterior surface and at least four conductive ink electrodes on the exterior surface, wherein the at least four conductive ink electrodes include at least two stimulating electrodes and at least two monitoring electrodes. At 1404, the method 1400 includes stimulating tissue of a patient with the stimulating electrodes, and monitoring at least one nerve of the patient using the monitoring electrodes during the stimulation.

The at least four conductive ink electrodes in method 1400 may be printed directly on the exterior surface of the endotracheal tube. The method 1400 may further include receiving, with the stimulating electrodes, a stimulation signal from a stimulation channel of a multi-channel nerve integrity monitor device. The method 1400 may further include sending, with the monitoring electrodes, a monitoring signal to a monitoring channel of the multi-channel nerve integrity monitor device. The method 1400 may further include carrying the stimulation signal and the monitoring signal between the electrodes and the multi-channel nerve integrity monitor device with a plurality of conductors. The method 1400 may further include analyzing, with a multi-channel nerve integrity monitor device, multiple channels of monitoring signals received from the monitoring electrodes; and identifying, with the multi-channel nerve integrity monitor device, a subset of the multiple channels to display based on the analysis. At least two of the at least four conductive ink electrodes may be laterally and longitudinally offset from other ones of the at least four conductive ink electrodes.

The method 1400 may further include positioning at least a portion of the endotracheal tube in a region of a trachea of the patient with at least some of the conductive ink electrodes in contact with at least a portion of the trachea; and stimulating vocal folds of the patient with the stimulating electrodes. The stimulating electrodes may include at least one automatic periodic stimulation (APS) electrode. The method 1400 may further include monitoring the at least one nerve of the patient using at least one of the stimulating electrodes.

Another embodiment is directed to a system, which includes an endotracheal tube having an exterior surface and at least four conductive ink electrodes on the exterior surface, wherein the at least four conductive ink electrodes include at least two stimulating electrodes configured to stimulate tissue of a patient, and wherein the at least four conductive ink electrodes include at least two monitoring electrodes configured to monitor at least one nerve of the patient. The system includes a multi-channel nerve integrity monitor device configured to send a stimulation signal to the stimulating electrodes via a first channel, and configured to receive a monitoring signal from the monitoring electrodes via a second channel.

The multi-channel nerve integrity monitor device may include at least four channels for sending stimulation signals to the stimulating electrodes and receiving monitoring signals from the monitoring electrodes. The multi-channel nerve integrity monitor device may be configured to analyze multiple channels of monitoring signals received from the monitoring electrodes, and identify a subset of the multiple channels to display based on the analysis. The at least four conductive ink electrodes may be printed directly on the exterior surface of the endotracheal tube. The system may further include a plurality of conductors configured to carry the stimulation signal and the monitoring signal between the electrodes and the multi-channel nerve integrity monitor device. At least two of the at least four conductive ink electrodes may be laterally and longitudinally offset from other ones of the at least four conductive ink electrodes. The stimulating electrodes may be configured to stimulate tissue in a region of vocal folds of the patient. The stimulating electrodes may include a first one of the stimulating electrodes that is laterally and longitudinally offset from a second one of the stimulating electrodes. The stimulating electrodes may include at least one automatic periodic stimulation (APS) electrode. At least one of the stimulating electrodes may also be configured to monitor the at least one nerve of the patient.

Yet another embodiment is directed to a system, which includes an endotracheal tube having an exterior surface and at least two laterally and longitudinally offset conductive ink electrodes on the exterior surface, wherein the at least two conductive ink electrodes include at least one stimulating electrode configured to stimulate tissue of a patient, and wherein the at least two conductive ink electrodes include at least one monitoring electrode configured to monitor at least one nerve of the patient. The system includes a nerve integrity monitor device configured to send a stimulation signal to the at least one stimulating electrode, and configured to receive a monitoring signal from the at least one monitoring electrode.

The at least one stimulating electrode may be configured to stimulate tissue in a region of vocal folds of the patient. The at least one stimulating electrode may include at least one automatic periodic stimulation (APS) electrode.

Yet another embodiment is directed to a multi-channel nerve integrity monitor device, which includes at least one stimulation channel configured to send a stimulation signal to at least one stimulating electrode to stimulate tissue of a patient; and a plurality of monitoring channels configured to receive a plurality of monitoring signals from a plurality of monitoring electrodes, wherein the nerve integrity monitor device is configured to analyze the plurality of monitoring signals received from the monitoring electrodes, and identify a subset of the plurality of monitoring signals to display based on the analysis.

Yet another embodiment is directed to a system, which includes an endotracheal tube having an exterior surface and a plurality of conductive ink electrodes on the exterior surface, wherein the conductive ink electrodes include a stimulating and monitoring electrode configured to stimulate tissue of a patient and monitor at least one nerve of the patient. The system includes a nerve integrity monitor device configured to send a stimulation signal to the stimulating and monitoring electrode, and configured to receive a monitoring signal from the stimulating and monitoring electrode.

Yet another embodiment is directed to a system, which includes an endotracheal tube having an exterior surface and a plurality of conductive ink electrodes on the exterior surface, wherein the conductive ink electrodes include a stimulating and monitoring electrode, which is a single electrode configured to both stimulate tissue of a patient and monitor at least one nerve of the patient. The system includes a nerve integrity monitor device configured to send a stimulation signal to the stimulating and monitoring electrode and configured to receive a monitoring signal from the stimulating and monitoring electrode. Some embodiments may include multiple stimulating and monitoring electrodes, wherein each of the stimulating and monitoring electrodes is a single electrode configured to both stimulate tissue of a patient and monitor at least one nerve of the patient.

Yet another embodiment is directed to a system, which includes an endotracheal tube having a plurality of electrodes, wherein the electrodes include at least one stimulating electrode configured to stimulate tissue of a patient and at least one monitoring electrode configured to monitor at least one nerve of a patient. The system includes a nerve integrity monitor device configured to send a stimulation signal to the at least one stimulating electrode to evoke a reflex response, and configured to receive a monitoring signal from the at least one monitoring electrode.

Yet another embodiment is directed to an endotracheal tube apparatus, which includes an endotracheal tube having at least one stimulating electrode configured to stimulate tissue of a patient; and a battery-powered module positioned on the endotracheal tube that is configured to send stimulation signals to the at least one stimulating electrode to evoke a reflex response by the patient.

The battery-powered module of the endotracheal tube apparatus may include a processor configured to generate digital stimulation signals. The module may include a digital-to-analog converter configured to convert the digital stimulation signals to analog stimulation signals that are sent to the at least one stimulating electrode. The module may be configured to sense the reflex response. The module may include an accelerometer to facilitate the sensing of the reflex response.

The endotracheal tube may include at least one monitoring electrode configured to monitor at least one nerve of the patient. The at least one monitoring electrode may be configured to send an analog monitoring signal to the module. The module may include an analog-to-digital converter to convert the analog monitoring signal into a digital monitoring signal. The module may include a processor to process the digital monitoring signal.

The module of the endotracheal tube apparatus may be configured to provide automatic periodic stimulation (APS) signals to the at least one stimulating electrode. The module may be configured to provide an alert signal to indicate degraded nerve function. The alert signal may be one of an audible, visual, or haptic alert signal. The at least one stimulating electrode may be configured to stimulate a laryngeal mucosa of the patient. The module may be configured to wirelessly communicate with a probe device. The module may be configured to wirelessly communicate with a nerve integrity monitor apparatus.

Figure 15:
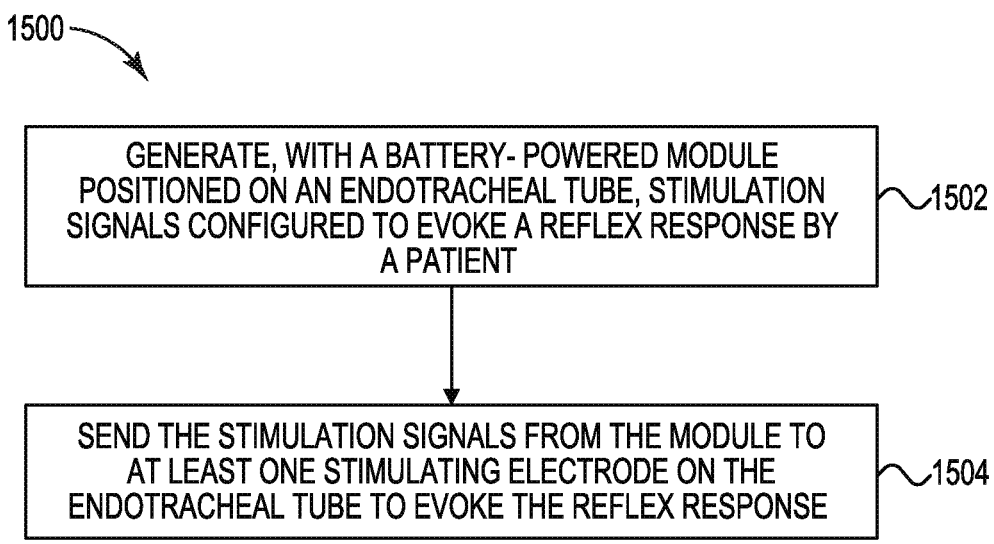
FIG. 15 is a flow diagram illustrating a method of evoking a reflex response with an endotracheal tube according to one embodiment.

Yet another embodiment is directed to a method of evoking a reflex response with an endotracheal tube. FIG. 15 is a flow diagram illustrating a method 1500 of evoking a reflex response with an endotracheal tube according to one embodiment. At 1502, the method 1500 includes generating, with a battery-powered module positioned on an endotracheal tube, stimulation signals configured to evoke a reflex response by a patient. At 1504, the stimulation signals are sent from the module to at least one stimulating electrode on the endotracheal tube to evoke the reflex response.

The method 1500 may further include sensing the reflex response with the module. The method 1500 may further include wirelessly transmitting information from the module to one of a probe device and a nerve integrity monitor apparatus.

Yet another embodiment is directed to an endotracheal tube apparatus, which includes an endotracheal tube having an exterior surface, and first and second laterally offset monitoring electrodes positioned on the exterior surface and configured to monitor at least one nerve of a patient. The endotracheal tube apparatus also includes a stimulating electrode positioned between the first and second monitoring electrodes on the exterior surface and configured to stimulate tissue of the patient to evoke a reflex response.

The first and second monitoring electrodes may be laterally and longitudinally offset and are positioned on a same side of the endotracheal tube as the stimulating electrode. The stimulating electrode may have a sinusoidal shape. The apparatus may further include a balloon cuff positioned longitudinally distal to the monitoring electrodes and the stimulating electrode. The monitoring electrodes and the stimulating electrode may be conductive ink electrodes.

The endotracheal tube apparatus may further include first, second, and third conductive traces respectively coupled to the first monitoring electrode, the second monitoring electrode, and the stimulating electrode. The first and second conductive traces may carry monitoring signals from the first and second monitoring electrodes to a processing device. The third conductive trace may carry stimulation signals from the processing device to the stimulating electrode. The processing device may be positioned on the endotracheal tube apparatus.

Figure 16:
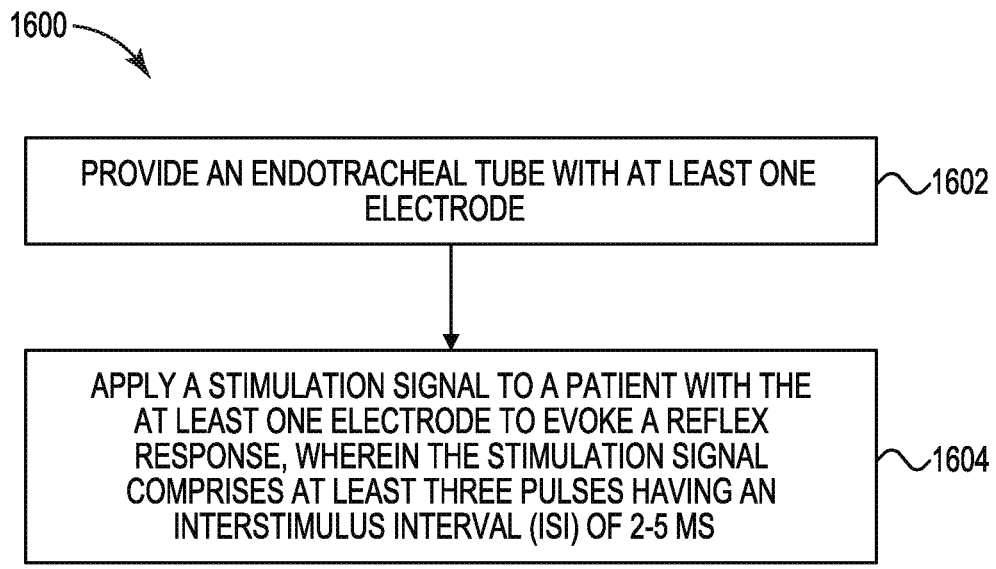
FIG. 16 is a flow diagram illustrating a method of evoking a reflex response with an endotracheal tube according to another embodiment.

Yet another embodiment is directed to a method of evoking a reflex response with an endotracheal tube. FIG. 16 is a flow diagram illustrating a method 1600 of evoking a reflex response with an endotracheal tube according to another embodiment. At 1602, the method 1600 includes providing an endotracheal tube with at least one electrode. At 1604, a stimulation signal is applied to a patient with the at least one electrode to evoke a reflex response, wherein the stimulation signal comprises at least three pulses having an interstimulus interval (ISI) of 2-5 ms.

The at least three pulses in the method 1600 may have an intensity of greater than 15 mA. The at least three pulses may have an intensity of greater than 20 mA. The ISI may be greater than 4 ms and less than or equal to 5 ms. The stimulation signal may include at least four pulses having an interstimulus interval (ISI) of 2-5 ms. The stimulation signal may include at least five pulses having an interstimulus interval (ISI) of 2-5 ms.

The stimulation signal in the method 1600 may be a double train stimulation signal in which the at least three pulses are followed less than one second later by at least three more pulses having an ISI of 2-5 ms. The stimulation signal may include a pre-stimulation tetanic stimulation that precedes the at least three pulses. The tetanic stimulation may be performed at 30-60 Hz for 1-10 seconds. Each of the at least three pulses may have a pulse duration of less than 100 microseconds. The stimulation signal may be monophasic with a positive polarity. The stimulation signal may be monophasic with a negative polarity. The stimulation signal may be biphasic. The stimulation signal may be generated by a battery-powered module positioned on the endotracheal tube.

The at least one electrode in the method 1600 may include a monitoring electrode, and the method 1600 may further include monitoring at least one nerve of the patient with the at least one monitoring electrode. The monitoring electrode may also be configured to apply the stimulation signal.

Yet another embodiment is directed to an endotracheal tube apparatus, which includes an endotracheal tube having an external surface; and at least one electrode positioned on the external surface, wherein the at least one electrode is configured to apply a stimulation signal, including at least three pulses having an interstimulus interval (ISI) of 2-5 ms, to a laryngeal mucosa of a patient to evoke a reflex response.

The endotracheal tube apparatus may further include a battery-powered module positioned on the endotracheal tube to generate the stimulation signal. The module may be configured to sense the reflex response. The module may include an accelerometer to facilitate the sensing of the reflex response. The at least one electrode may include an electrode that is configured to both apply the stimulation signal and monitor at least one nerve of the patient. The stimulation signal may be generated by a nerve integrity monitor (NIM) apparatus, and the endotracheal tube apparatus may further include at least one conductor configured to deliver the stimulation signal from the NIM apparatus to the at least one electrode.

The endotracheal tube apparatus may further include first and second monitoring electrodes positioned on the external surface on a first side of the endotracheal tube, and the at least one electrode that is configured to apply the stimulation signal may be positioned on the first side of the endotracheal tube between the first and the second monitoring electrodes. In another embodiment, the endotracheal tube apparatus may include a monitoring electrode positioned on the external surface on a first side of the endotracheal tube, and the at least one electrode that is configured to apply the stimulation signal may be positioned on a second side opposite the first side of the endotracheal tube.

Figure 17:
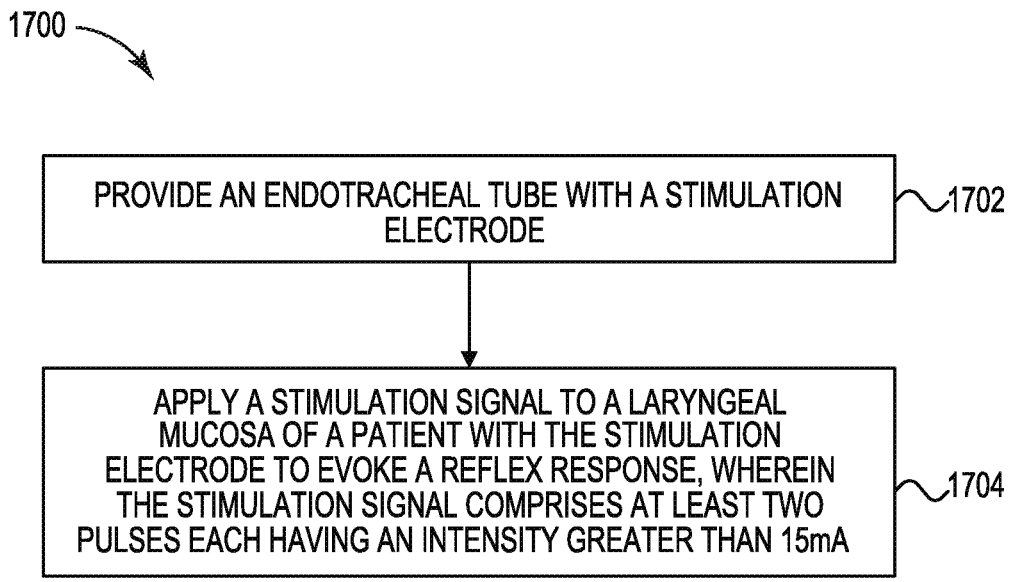
FIG. 17 is a flow diagram illustrating a method of evoking a reflex response with an endotracheal tube according to another embodiment.

Yet another embodiment is directed to a method of evoking a reflex response with an endotracheal tube. FIG. 17 is a flow diagram illustrating a method 1700 of evoking a reflex response with an endotracheal tube according to another embodiment. At 1702, the method 1700 includes providing an endotracheal tube with a stimulation electrode. At 1704, a stimulation signal is applied to a laryngeal mucosa of a patient with the stimulation electrode to evoke a reflex response, wherein the stimulation signal comprises at least two pulses each having an intensity greater than 15 mA.

The at least two pulses in the method 1700 may each have an intensity greater than 20 mA. The stimulation signal may include at least three pulses having an interstimulus interval (ISI) of 2-5 ms and each having an intensity greater than 15 mA.

Although the present disclosure has been described with reference to preferred embodiments, workers skilled in the art will recognize that changes can be made in form and detail without departing from the spirit and scope of the present disclosure.

What is claimed is:

1. A method, comprising:
providing an endotracheal tube with at least one electrode; and
applying a stimulation signal to a laryngeal mucosa of a patient with the at least one electrode of the endotracheal tube to evoke a laryngeal reflex response, wherein the stimulation signal comprises at least three pulses having an interstimulus interval (ISI) of 2-5 ms.

2. The method of claim 1, wherein the at least three pulses have an intensity of greater than 15 mA.

3. The method of claim 1, wherein the at least three pulses have an intensity of greater than 20 mA.

4. The method of claim 1, wherein the ISI is greater than 4 ms and less than or equal to 5 ms.

5. The method of claim 1, wherein the stimulation signal comprises at least four pulses having an interstimulus interval (ISI) of 2-5 ms.

6. The method of claim 1, wherein the stimulation signal comprises at least five pulses having an interstimulus interval (ISI) of 2-5 ms.

7. The method of claim 1, wherein the stimulation signal is a double train stimulation signal in which the at least three pulses are followed less than one second later by at least three more pulses having an ISI of 2-5 ms.

8. The method of claim 1, wherein the stimulation signal includes a pre-stimulation tetanic stimulation that precedes the at least three pulses.

9. The method of claim 8, wherein the tetanic stimulation is performed at 30-60 Hz for 1-10 seconds.

10. The method of claim 1, wherein each of the at least three pulses has a pulse duration of less than 100 microseconds.

11. The method of claim 1, wherein the stimulation signal is monophasic with a positive polarity.

12. The method of claim 1, wherein the stimulation signal is monophasic with a negative polarity.

13. The method of claim 1, wherein the stimulation signal is biphasic.

14. The method of claim 1, wherein the stimulation signal is generated by a battery-powered module positioned on the endotracheal tube.

15. The method of claim 14, wherein the endotracheal tube includes a monitoring electrode, and wherein the method further comprises:
monitoring at least one nerve of the patient with the monitoring electrode.

16. The method of claim 15, wherein the monitoring electrode is also configured to apply the stimulation signal.

17. A method, comprising: providing an endotracheal tube with a stimulation electrode; and applying a stimulation signal to a laryngeal mucosa of a patient with the stimulation electrode of the endotracheal tube to evoke a laryngeal reflex response, wherein the stimulation signal comprises at least three pulses having an interstimulus interval (ISI) of 2-5 ms and each having an intensity greater than 15 mA.

18. The method of claim 17, wherein the laryngeal reflex response is one of a pharyngeal gag reflex, a pharyngoglottal closure reflex, or a Hoffman reflex.

19. The method of claim 17, wherein the at least three pulses each have an intensity greater than 20 mA.

20. The method of claim 1, wherein the laryngeal reflex response is one of a pharyngeal gag reflex, a pharyngoglottal closure reflex, or a Hoffman reflex.

\* \* \* \* \*